(12) United States Patent
Fujita

(10) Patent No.: US 10,413,160 B2
(45) Date of Patent: Sep. 17, 2019

(54) FIBER SENSOR SYSTEM

(71) Applicant: Olympus Corporation, Hachioji-shi, Tokyo (JP)

(72) Inventor: Hiromasa Fujita, Hachioji (JP)

(73) Assignee: Olympus Corporation, Tokyo (JP)

( * ) Notice: Subject to any disclaimer, the term of this patent is extended or adjusted under 35 U.S.C. 154(b) by 96 days.

(21) Appl. No.: 15/653,981

(22) Filed: Jul. 19, 2017

(65) Prior Publication Data

US 2017/0311775 A1 Nov. 2, 2017

Related U.S. Application Data

(63) Continuation of application No. PCT/JP2015/051699, filed on Jan. 22, 2015.

(51) Int. Cl.
*A61B 1/00* (2006.01)
*A61B 1/005* (2006.01)
*G01D 5/26* (2006.01)
*G02B 23/26* (2006.01)
(Continued)

(52) U.S. Cl.
CPC .......... *A61B 1/00013* (2013.01); *A61B 1/005* (2013.01); *A61B 1/00016* (2013.01); *A61B 1/00154* (2013.01); *A61B 1/00165* (2013.01); *G01D 5/268* (2013.01); *G01D 5/35316* (2013.01); *G01D 5/35361* (2013.01); *G01D 5/35364* (2013.01); *G01D 21/00* (2013.01);
(Continued)

(58) Field of Classification Search
CPC ............ A61B 1/00013; A61B 1/00016; A61B 1/00154; A61B 1/005; A61B 1/00165; A61B 1/00029; A61B 1/00057; G01D 21/00; G01D 5/35361; G01D 5/35316; G01D 5/35364; G01D 5/268; G02B 23/26
See application file for complete search history.

(56) References Cited

U.S. PATENT DOCUMENTS

| 5,840,024 A | 11/1998 | Taniguchi et al. |
| 6,059,718 A | 5/2000 | Taniguchi et al. |
| 2010/0099951 A1 | 4/2010 | Laby et al. |

(Continued)

FOREIGN PATENT DOCUMENTS

| JP | 11-211997 A | 8/1999 |
| JP | 2003275164 | 9/2003 |

(Continued)

OTHER PUBLICATIONS

English Translation of International Search Report and Written Opinion dated Apr. 21, 2015 issued in PCT/JP2015/051699, 10 pages.

(Continued)

*Primary Examiner* — Tony Ko
(74) *Attorney, Agent, or Firm* — Matthew M. Eslami

(57) ABSTRACT

A system comprises a housing, a light source, a light guide configured to guide a light from the light source. The light guide includes a plurality of detection target configured to provide optical effect on the light in accordance with a bend state of the light guide. A light detector is configured to detect the light emitted from the light guide and provide information of the detected light. A communication unit is configured to transmit wirelessly the information of the detected light. The communication unit is disposed in the housing.

16 Claims, 14 Drawing Sheets

(51) Int. Cl.
  *G01D 5/353* (2006.01)
  *G01D 21/00* (2006.01)
(52) U.S. Cl.
  CPC .......... *G02B 23/26* (2013.01); *A61B 1/00029* (2013.01); *A61B 1/00057* (2013.01)

(56) References Cited

U.S. PATENT DOCUMENTS

| | | |
|---|---|---|
| 2011/0098533 A1 | 4/2011 | Onoda et al. |
| 2011/0172519 A1 | 7/2011 | Cao et al. |
| 2012/0259211 A1 | 10/2012 | Cao et al. |
| 2013/0325387 A1 | 12/2013 | Manzke et al. |
| 2014/0316193 A1 | 10/2014 | Taniguchi |
| 2014/0330080 A1 | 11/2014 | Laby et al. |
| 2015/0305597 A1 | 10/2015 | Ito et al. |
| 2016/0073866 A1* | 3/2016 | Fujita ................ A61B 1/00112 600/117 |

FOREIGN PATENT DOCUMENTS

| | | |
|---|---|---|
| JP | 2011-500162 A | 1/2011 |
| JP | 2013-106752 A | 6/2013 |
| JP | 2014-064917 A | 4/2014 |
| JP | 2014-508582 A | 4/2014 |
| JP | 2014-113352 A | 6/2014 |
| JP | 2014-226415 A | 12/2014 |
| WO | WO 2009-049038 A | 4/2009 |
| WO | WO 2010-050526 A | 5/2010 |
| WO | WO 2012-101555 A | 8/2012 |
| WO | WO 2014-061458 A | 4/2014 |

OTHER PUBLICATIONS

Office action dated Jul. 31, 2018 for the corresponding Japanese application JP2016-570427.
Office Action from corresponding Japanese application JP2016-570427, dated May 7. 2019.

* cited by examiner

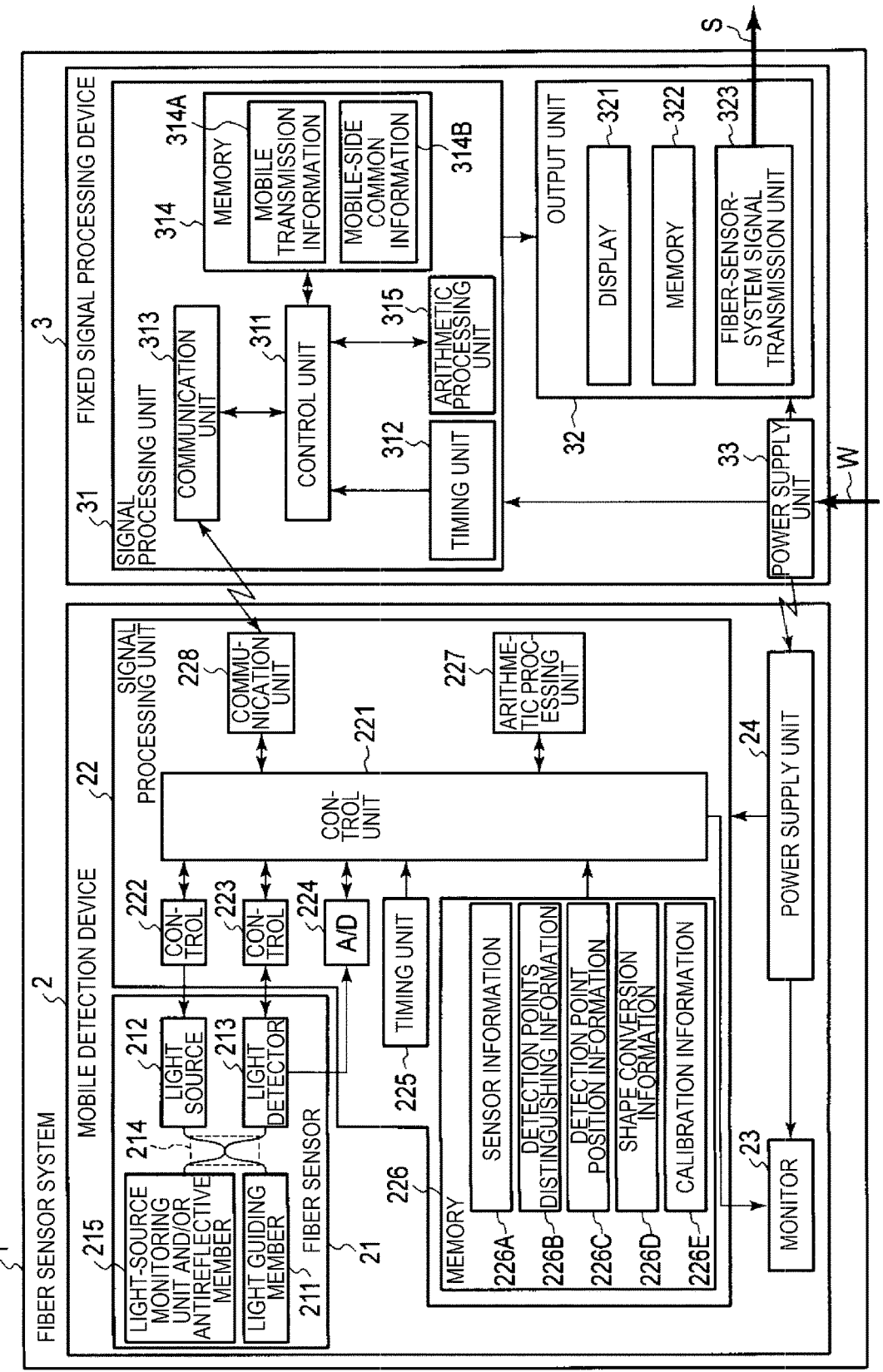
[FIG. 1]

[FIG. 2A]
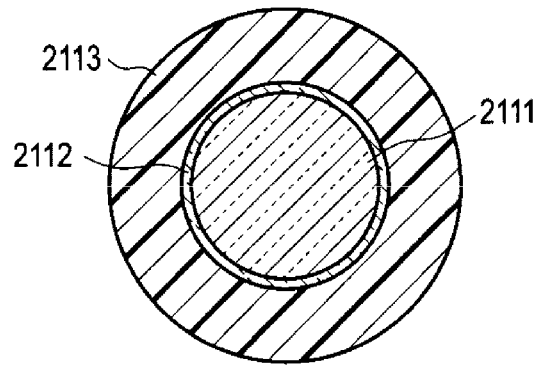
[FIG. 2B]
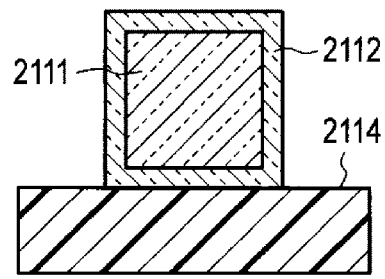
[FIG. 3A]
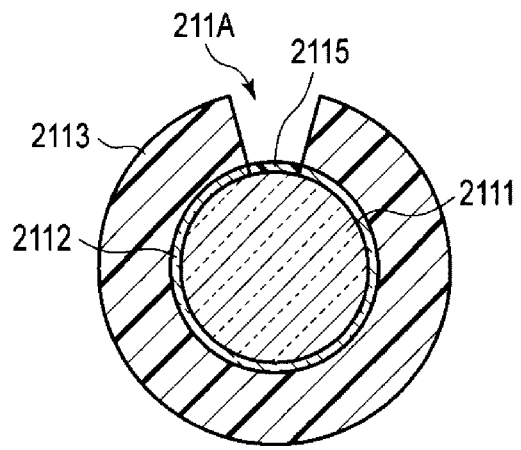

[FIG. 3B]
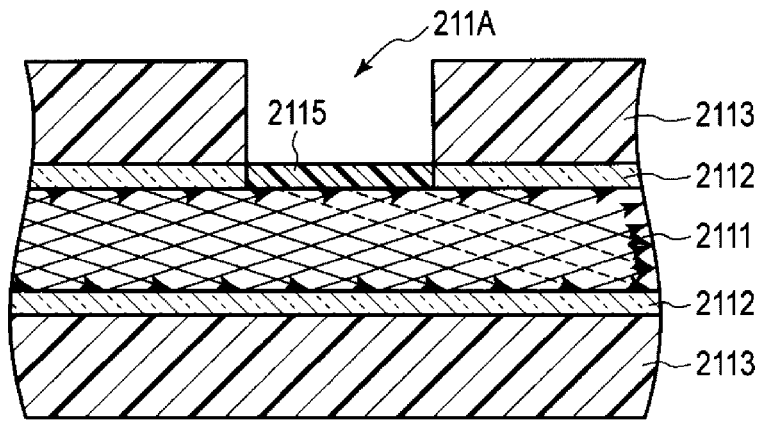
[FIG. 4A]
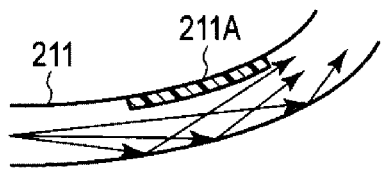
[FIG. 4B]
[FIG. 4C]
[FIG. 5A]
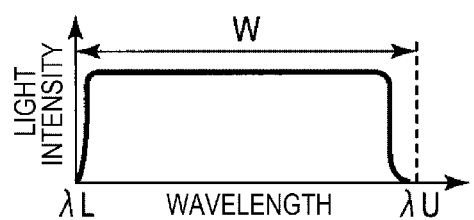

[FIG. 5B]
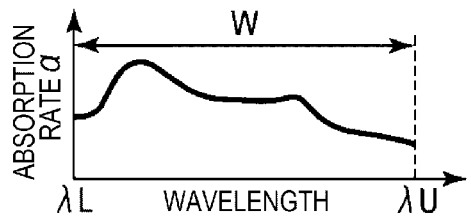
[FIG. 5C]
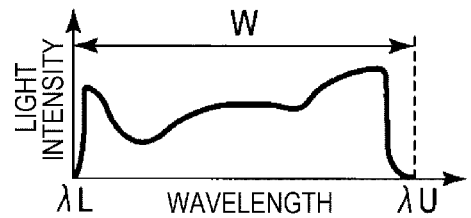
[FIG. 6A]
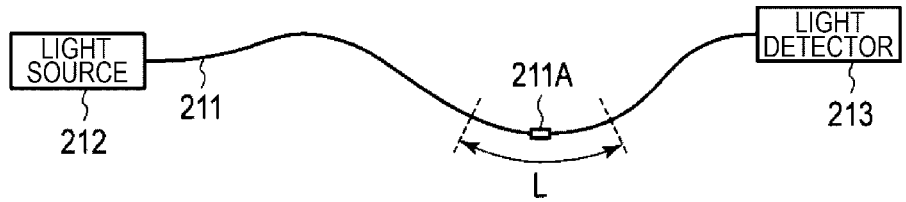
[FIG. 6B]
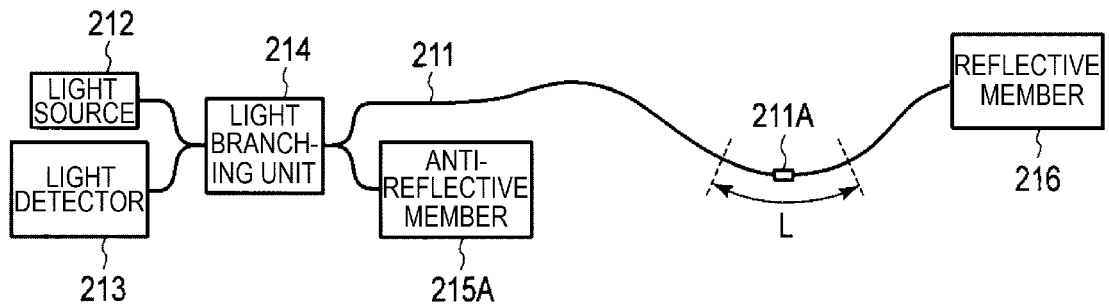

[FIG. 7A]
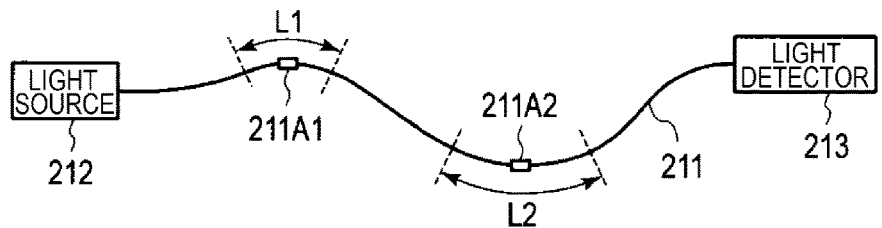
[FIG. 7B]
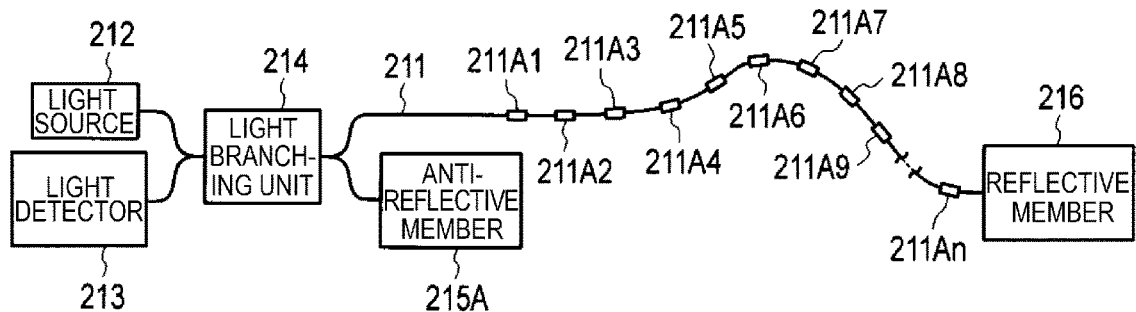
[FIG. 8]
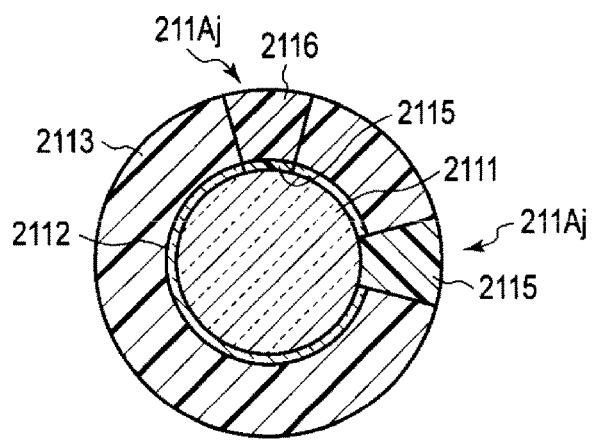

[FIG. 9A]
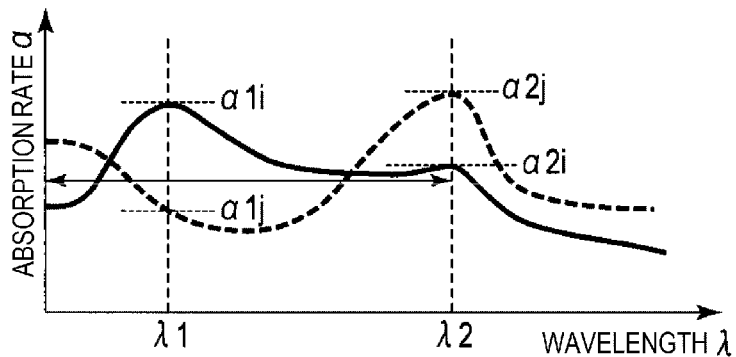
[FIG. 9B]
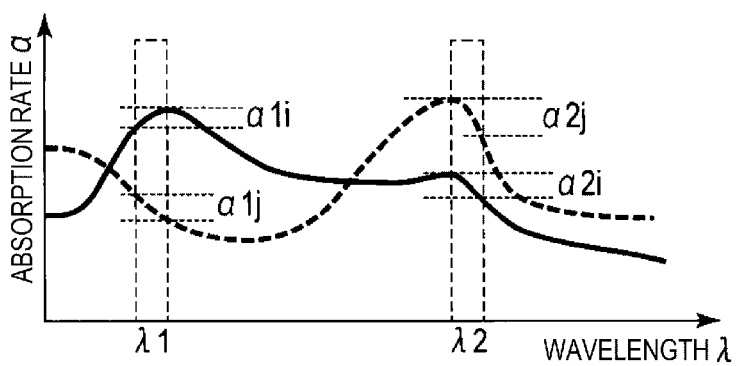
[FIG. 10A]
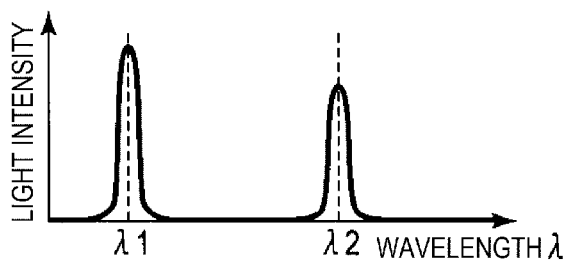
[FIG. 10B]
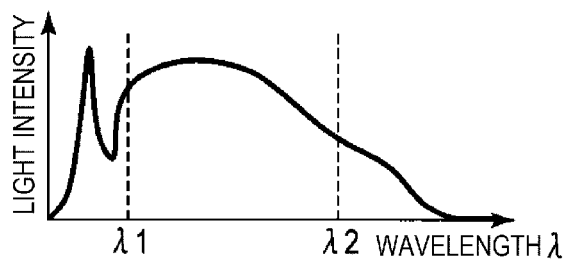

[FIG. 10C]
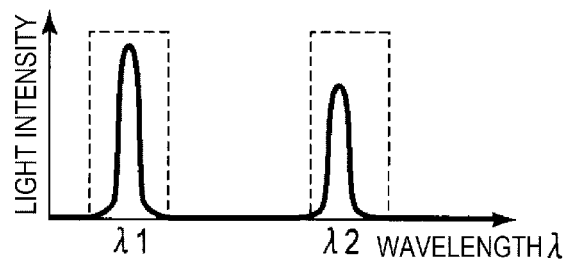
[FIG. 10D]
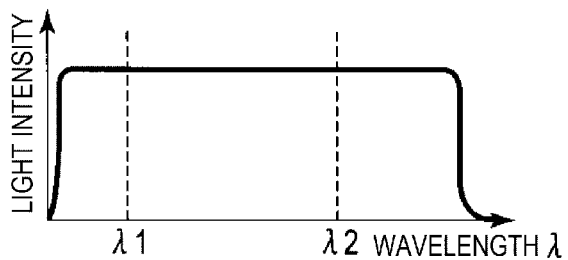
[FIG. 11A]
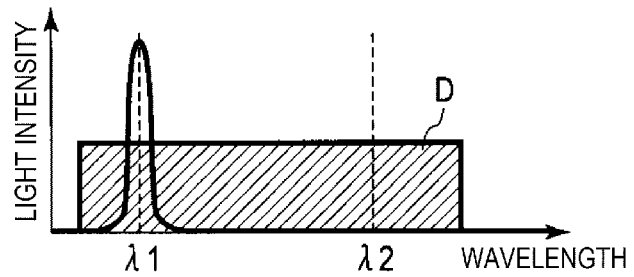
[FIG. 11B]
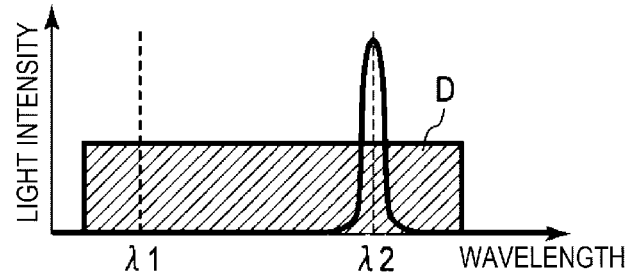

[FIG. 12A]
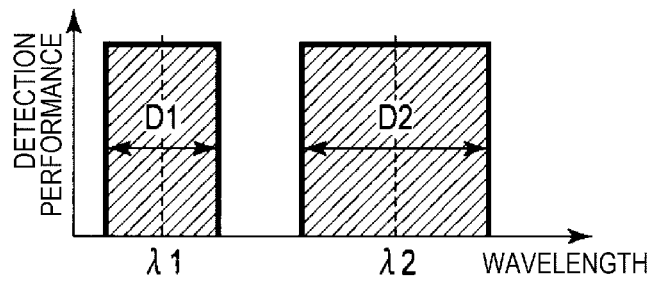
[FIG. 12B]
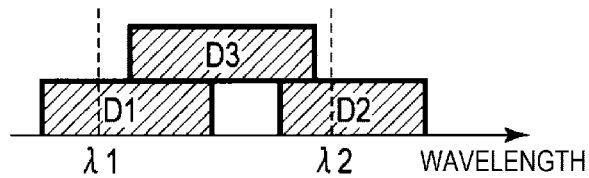
[FIG. 13A]
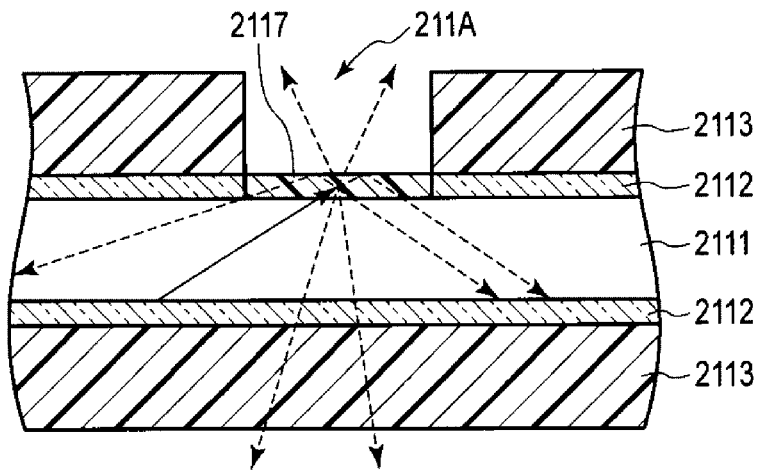
[FIG. 13B]
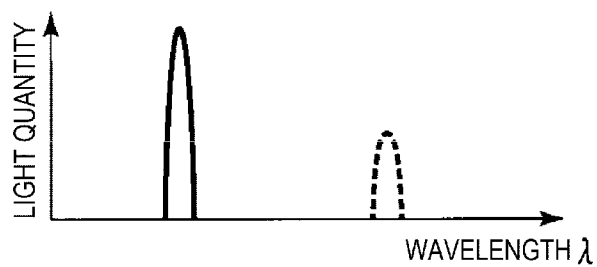

[FIG. 14]
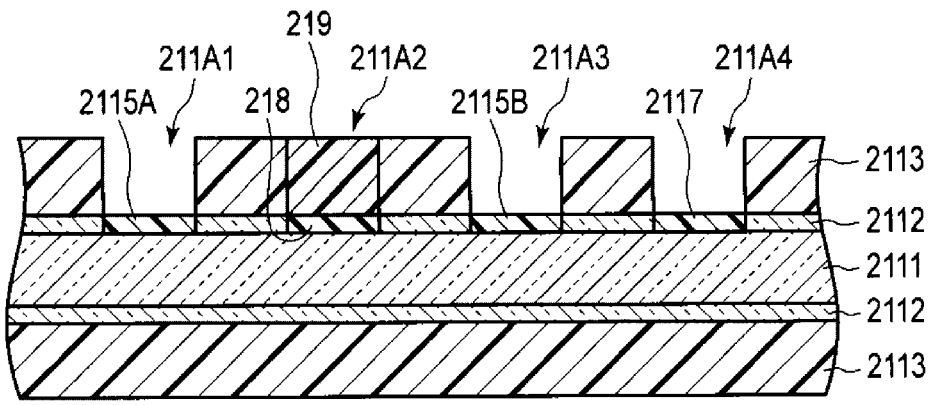
[FIG. 15]
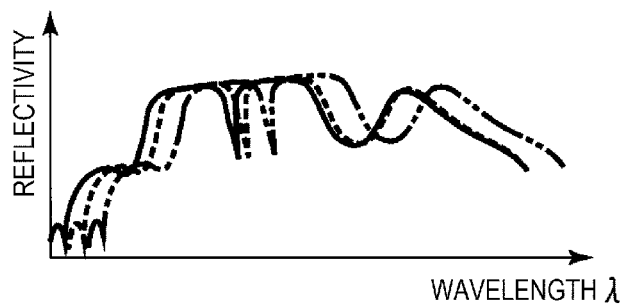
[FIG. 16A]
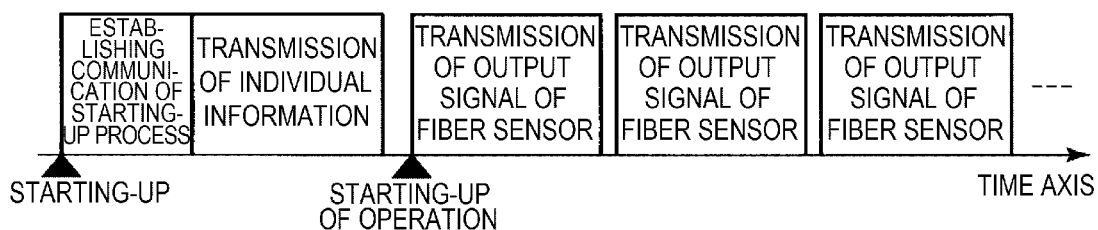
[FIG. 16B]
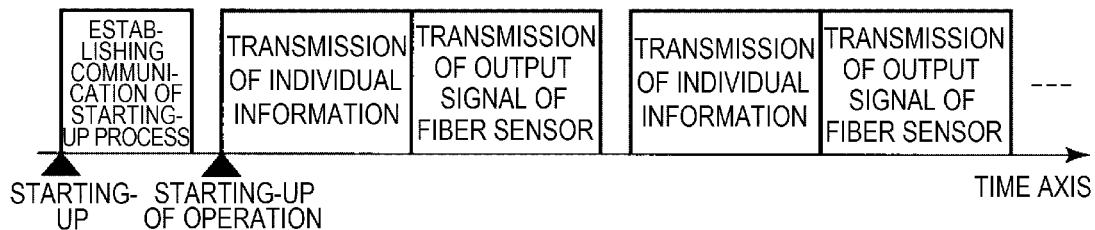

[FIG. 16C]
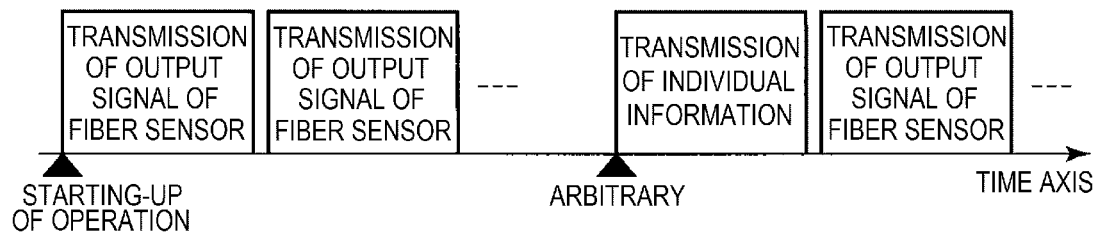
[FIG. 17]
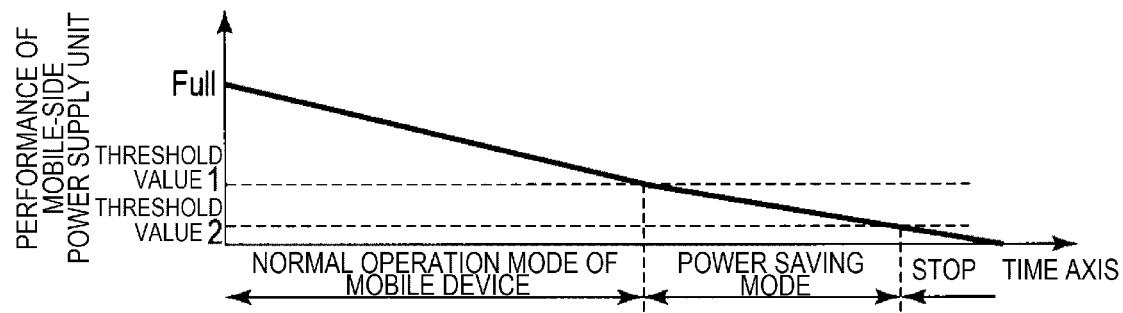

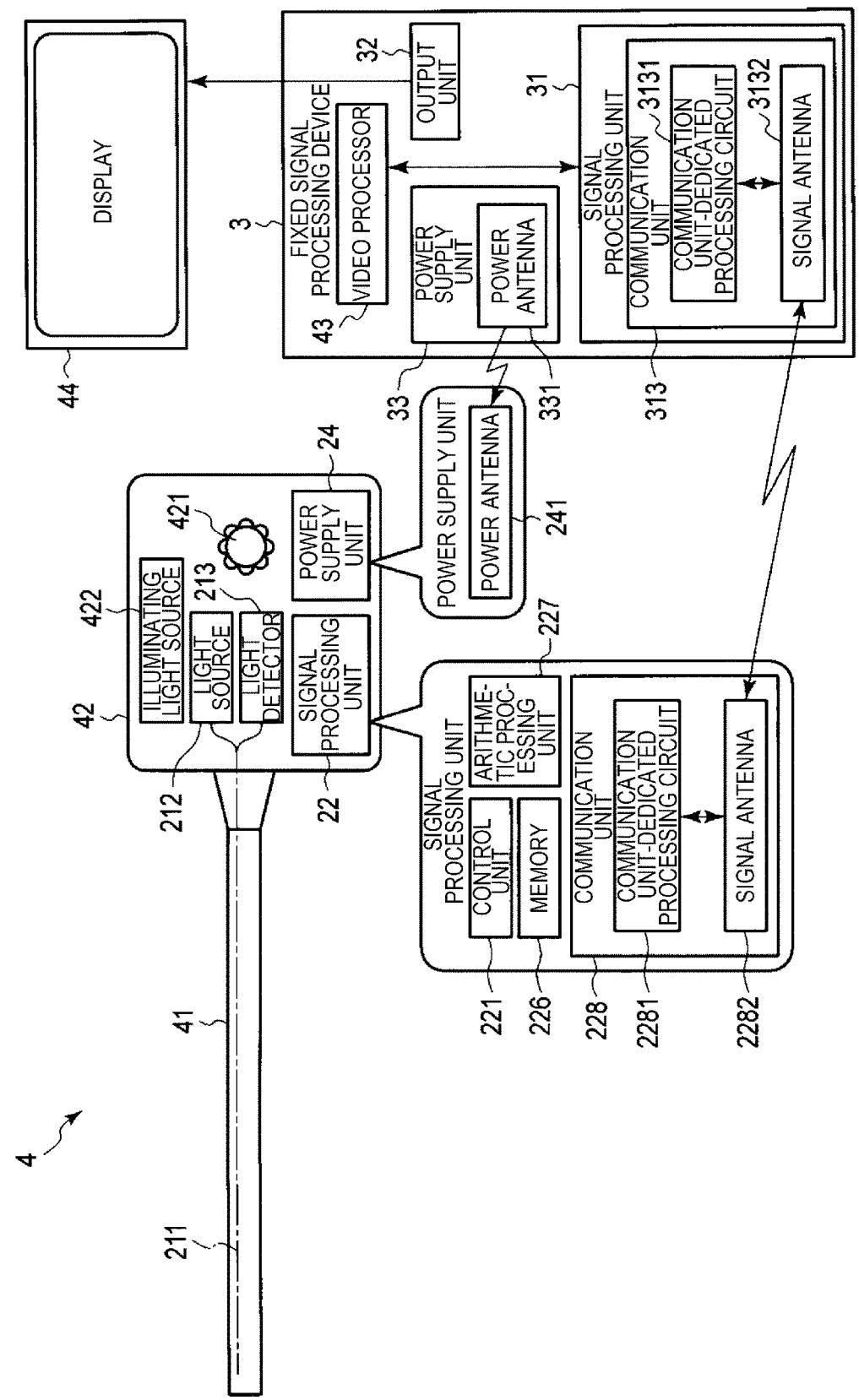
[FIG. 18]

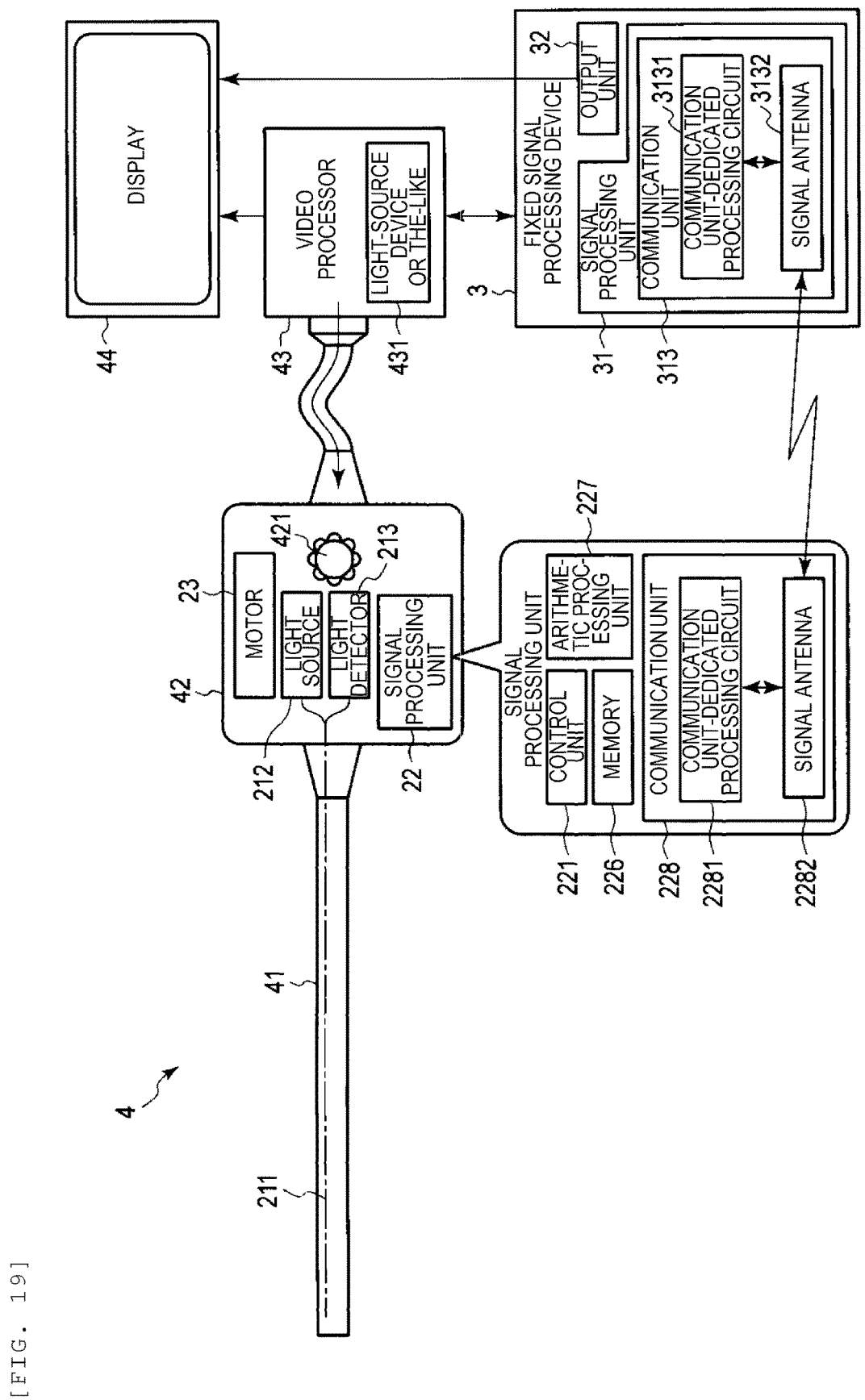
[FIG. 19]

[FIG. 20]
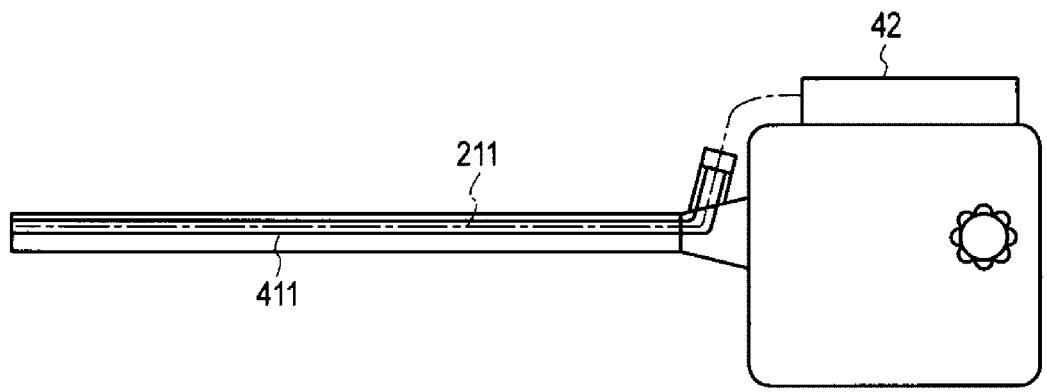
[FIG. 21A]
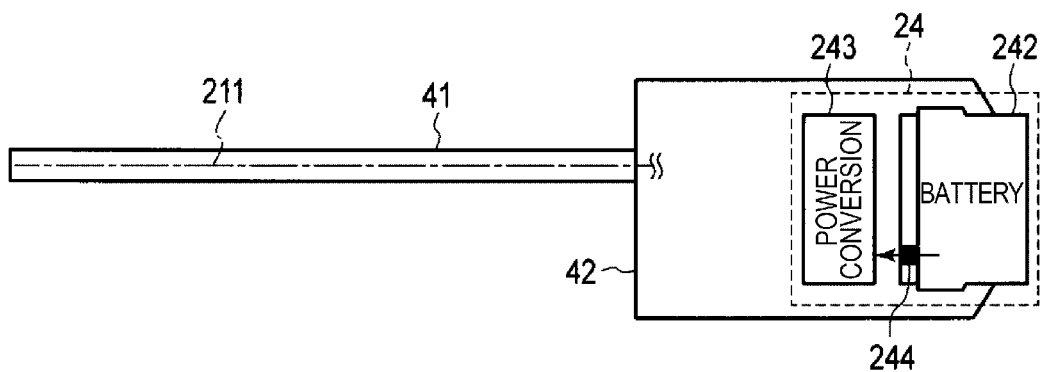
[FIG. 21B]
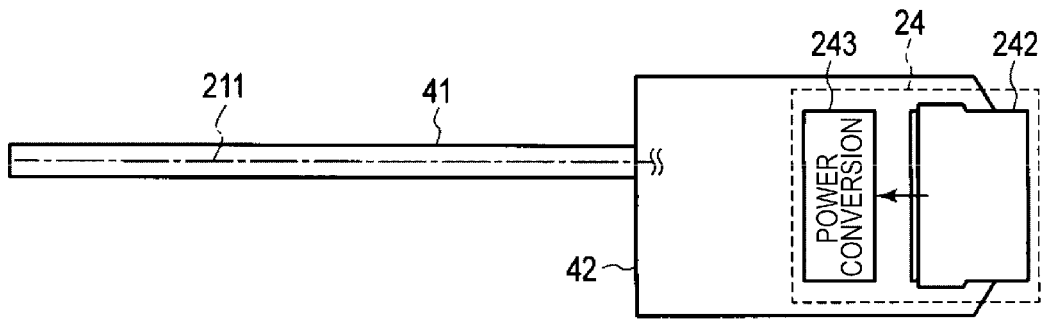

[FIG. 22]
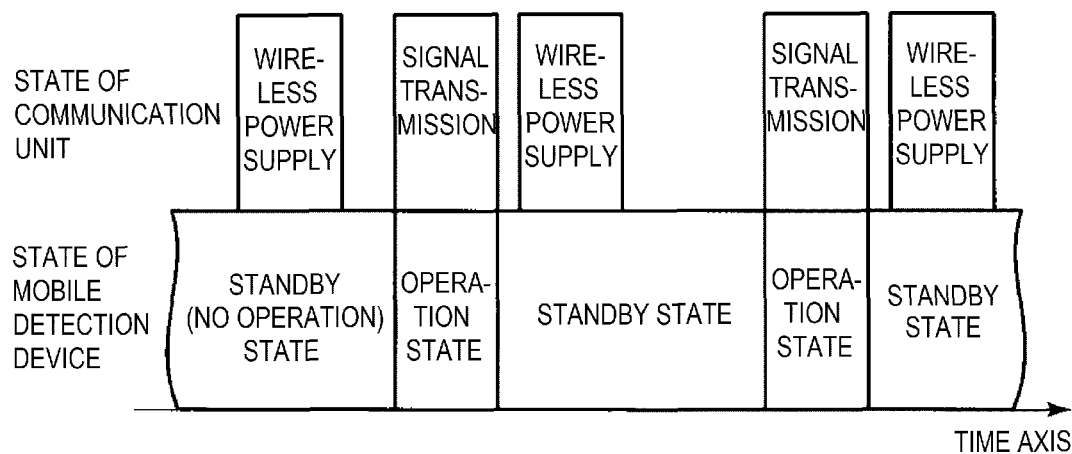
[FIG. 23]
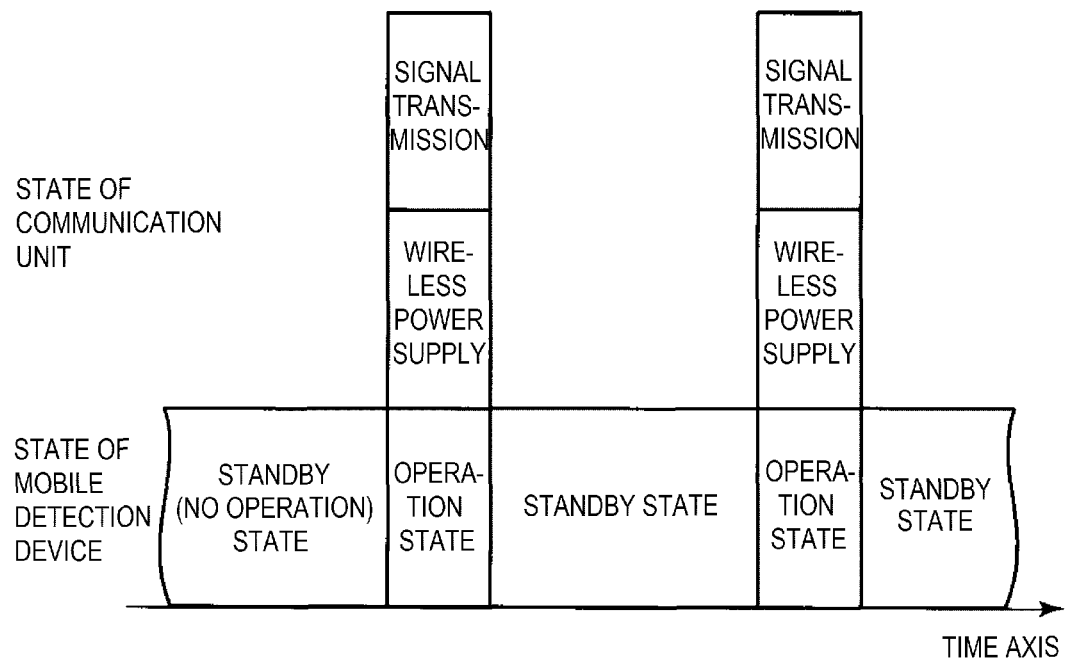

FIBER SENSOR SYSTEM

CROSS-REFERENCE TO RELATED APPLICATION(S)

This application is a continuation application of PCT Application No. PCT/JP2015/051699 filed Jan. 22, 2015, which is hereby incorporated by reference in its entirety.

TECHNICAL FIELD

The present invention relates to a fiber sensor system that detects a bending shape of a detection target portion on an optical fiber, and an endoscope device equipped with the fiber sensor system.

BACKGROUND

A conventional system for detecting a shape of an insertion portion of an endoscope may be equipped with a FBG (fiber sensor that detects distortion using an amount of wavelength shift). The conventional system has a configuration in which a cable extending from the endoscope is connected to an optical connector provided in a shape detection device which is separately configured from the endoscope, and thereby a light signal from the FBG sensor is transmitted to the shape detection device. Therefore, the shape detection device is equipped with a light source (tunable laser) and a detector.

SUMMARY

Example embodiments of the present invention relate to a system. In one aspect the system comprises a housing, a light source, a light guide configured to guide a light from the light source, the light guide having a plurality of detection target configured to provide optical effect on the light in accordance with a bend state of the light guide, a light detector configured to detect the light emitted from the light guide and provide information of the detected light, and a communication unit configured to transmit wirelessly the information of the detected light, the communication unit being disposed in the housing.

In another aspect the system comprises a housing, a light source, a light guide configured to guide a light from the light source, the light guide having a plurality of detection target configured to provide optical effect on the light in accordance with a bend state of the light guide, a light detector configured to detect the light emitted from the light guide and provide information of the detected light, a processor enabled to calculate an intermediate processing information relating to the bend state of the light guide, and a communication unit configured to transmit wirelessly the intermediate processing information, and the communication unit being disposed in the housing.

In another aspect the system comprises a housing, a light source, a light guide configured to guide a light from the light source, the light guide having a plurality of detection target configured to provide optical effect on the light in accordance with a bend state of the light guide, a light detector configured to detect the light emitted from the light guide and provide information of the detected light, a processor enabled to calculate the bend state of the light guide based on the detected light, and a communication unit configured to transmit wirelessly the bend state, and the communication unit being disposed in the housing.

BRIEF DESCRIPTION OF DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every Figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompanying drawings in which:

FIG. 1 is a block diagram illustrating a schematic configuration of a fiber sensor system according to an embodiment of the present invention.

FIG. 2A is a sectional view illustrating a shape of an example of a light guiding member.

FIG. 2B is a sectional view illustrating a shape of another example of the light guiding member.

FIG. 3A is a sectional view illustrating an example of a configuration of a detection target portion in the light guiding member in FIG. 2A.

FIG. 3B is a sectional view taken along a longitudinal direction of the detection target portion region in the light guiding member in FIG. 3A.

FIG. 4A is a diagram illustrating a case where the light guiding member bends on an upper side of paper, in order to describe principles of the fiber sensor.

FIG. 4B is a diagram illustrating a case where the light guiding member does not bend, in order to describe the principles of the fiber sensor.

FIG. 4C is a diagram illustrating a case where the light guiding member bends on a lower side of paper, in order to describe the principles of the fiber sensor.

FIG. 5A is a diagram illustrating an example of a spectrum of light that is incident to the light guiding member.

FIG. 5B is a diagram illustrating an example of an absorption spectrum of an absorption-wavelength-specific-region generating member disposed on the detection target portion.

FIG. 5C is a diagram illustrating an example of a spectrum of light that is emitted from the light guiding member.

FIG. 6A is a diagram for describing a configuration of a transmission type fiber sensor.

FIG. 6B is a diagram for describing a configuration of a reflection type fiber sensor.

FIG. 7A is a diagram for describing a configuration of a transmission type fiber sensor that is provided with a plurality of detection target portions.

FIG. 7B is a diagram for describing a configuration of a reflection type fiber sensor that is provided with a plurality of detection target portions.

FIG. 8 is a sectional view illustrating another example of a configuration of a detection target portion in the light guiding member.

FIG. 9A is a diagram for describing absorption wavelength specific regions in a plurality of absorption-wavelength-specific-region generating members disposed on the detection target portion.

FIG. 9B is a diagram for describing another example of the absorption wavelength specific region.

FIG. 10A is a diagram illustrating a relationship between a spectrum of light from an ideal light source and the absorption wavelength specific region.

FIG. 10B is a diagram illustrating a relationship between a spectrum of light from a light source that emits discrete light and the absorption wavelength specific region.

FIG. 10C is a diagram illustrating a relationship between a spectrum of light from a light source that emits light having continuous wavelength spectrum and the absorption wavelength specific region.

FIG. 10D is a diagram illustrating a relationship between a spectrum of light from the light source in FIG. 10B and another example of an absorption wavelength specific region.

FIG. 11A is a diagram for describing a detection band of a light detector with respect to a spectrum of a light source.

FIG. 11B is a diagram for describing the detection band of the light detector with respect to a spectrum of another light source.

FIG. 12A is a diagram illustrating an example of a wavelength band of the light detector in a case of having two detection target portions.

FIG. 12B is a diagram illustrating an example of a wavelength band of the light detector in a case of having three detection target portions.

FIG. 13A is a sectional view of the light guiding member in a case of using a fluorescent member as another example of the detection target portion.

FIG. 13B is a diagram illustrating absorption characteristics and light emission characteristics of the fluorescent member.

FIG. 14 is a sectional view of the light guiding member in a case of using a plurality of absorption-wavelength-specific-region generating members, the fluorescent member, and a stacked dielectric membrane, as examples of the plurality of detection target portions.

FIG. 15 is a diagram illustrating an example of reflection spectral characteristics of the dielectric membrane.

FIG. 16A is a diagram illustrating a timing chart for describing an operation of the fiber sensor in a case where a transmission timing of fiber sensor individual information is the time of starting up.

FIG. 16B is a diagram illustrating a timing chart for describing an operation of the fiber sensor in a case where the transmission timing of the fiber sensor individual information is whenever an output signal of the fiber sensor is transmitted.

FIG. 16C is a diagram illustrating a timing chart for describing an operation of the fiber sensor in a case where the transmission timing of the fiber sensor individual information is an arbitrary time point in response to a request from a fixed signal processing device.

FIG. 17 is diagram for describing transition of operation modes of a mobile detection device.

FIG. 18 is a diagram for describing an example of a configuration in a case where an endoscope device is equipped with a fiber sensor system according to an embodiment.

FIG. 19 is a diagram for describing another example of the configuration in a case where an endoscope device is equipped with a fiber sensor system according to an embodiment.

FIG. 20 is a diagram for describing still another example of the configuration in a case where an endoscope device is equipped with a fiber sensor system according to an embodiment.

FIG. 21A is a diagram illustrating an example of a configuration of a power supply unit of the mobile detection device.

FIG. 21B is a diagram illustrating another example of the configuration of the power supply unit of the mobile detection device.

FIG. 22 is a diagram illustrating an example of an operation state of a communication unit of the mobile detection device.

FIG. 23 is a diagram illustrating another example of the operation state of the communication unit of the mobile detection device.

DETAILED DESCRIPTION

In the configuration in which the light signal from the fiber sensor is transmitted to an external device by the optical connector, problems arise in that a device such as an endoscope equipped with the fiber sensor has poor handling properties, a loss of the light signal occurs in an optical connector region, and it is difficult to detect a minute change in shape. In addition, the light signal has a spectral alteration in the optical connector region in some cases. In order to reliably and accurately detect a shape, an effect on the light signal from the fiber sensor, which is produced in the optical connector region, is not negligible.

The present invention is made in consideration of the circumstances described above, and objects thereof are to provide a fiber sensor system that is capable of reliably and accurately detecting a shape and an endoscope device equipped with the fiber sensor system.

According to the present invention, it is possible to provide a fiber sensor system that is capable of reliably and accurately detecting a shape and an endoscope device equipped with the fiber sensor system.

Hereinafter, an embodiment of the present invention will be described with reference to the figures.

A fiber sensor system 1 according to an embodiment of the present invention includes a mobile detection device 2 and a fixed signal processing device 3, as illustrated in FIG. 1. The mobile detection device 2 is a mobile device that is used along with movement through manipulation by a manipulator. The fixed signal processing device 3 is provided in a device or the like which is mounted on a rack such as a suspended rack from a ceiling or a trolley, or is embedded in a wall. The fixed signal processing device 3 can move with the rack moving before the manipulator of the mobile detection device 2 starts the manipulation, but is a fixed device of which the position does not change along with a manipulating operation of the mobile detection device 2.

The mobile detection device 2 and the fixed signal processing device 3 are used as a set; however, the devices can be used even when either one is replaced with another device. For example, a plurality of mobile detection devices 2 can be provided, and then it is possible to appropriately incorporate one mobile detection device into the fixed signal processing device 3. The incorporated mobile detection device 2 and the fixed signal processing device 3 are wirelessly connected to each other.

The mobile detection device 2 includes a fiber sensor 21, a signal processing unit 22, a monitor 23, and a power supply unit 24.

The fiber sensor 21 is configured to have a light guiding member 211, a light source 212, a light detector 213, a light branching unit 214, and a light-source monitoring unit and/or antireflective member 215.

Here, the light guiding member 211 is disposed to extend in a longitudinal axis direction of a mounting portion, for example, an insertion portion of an endoscope, of which a bending shape needs to be detected by the fiber sensor system 1, and the light guiding member has flexibility to bend following a bending state of the mounting portion.

Specifically, the light guiding member 211 can be configured of an optical fiber. FIG. 2A illustrates a cross-section structure in a radial direction as a direction orthogonal to the longitudinal axis direction of the optical fiber. In other words, the optical fiber is configured to have a core 2111 at the center thereof and guides light, a clad 2112 provided around the core 2111 and stably confine the light in the core 2111, and a jacket 2113 for protecting the core 2111 and the clad 2112 from physical impacts and thermal impacts.

Otherwise, the light guiding member 211 may be configured of an optical waveguide. As illustrated in FIG. 2B, the optical waveguide is formed to have the core 2111 and the clad 2112, which play the same roles in the optical fiber, on a flexible substrate 2114.

Hereinafter, the fiber sensor 21 will be further described using an example of a case in which the light guiding member 211 is configured of such an optical fiber.

The optical fiber as the light guiding member 211 of the fiber sensor 21 is provided with at least one detection target portion 211A as illustrated in FIGS. 3A and 3B at a position corresponding to a position of the mounting portion of which the bending shape needs to be detected. In other words, the detection target portion 211A is formed as follows. The jacket 2113 and the clad 2112 are removed and a part of the core 2111 is exposed at a desirable position on the optical fiber in the longitudinal axis direction thereof, and an absorption-wavelength-specific-region generating member 2115 for generating an absorption wavelength specific region is formed in a region on the exposed core 2111. The absorption-wavelength-specific-region generating member 2115 is formed to have about the same thickness as that of the clad. Note that the jacket 2113 and the clad 2112 are removed through a laser process, or a photolithography process, an etching process, and the like. At this time, when a micro scratch is produced in the core 2111, light leaks and a loss of the guided light occurs, or the optical fiber becomes weak against the bending. Therefore, it is desirable to perform a process in a way the core 2111 is not scratched as much as possible.

In such a detection target portion 211A, when the optical fiber as the light guiding member 211 bends, a very small part of light transmitting in the optical fiber leaks into the detection target portion 211A in response to the bending. In other words, the detection target portion 211A is provided on one side of the optical fiber and an amount of the light leak (light in a degree of seeping out) changes depending on the bending of the optical fiber. In other words, the detection target portion 211A is formed by changing optical characteristics, for example, a light transmission amount, of the optical fiber.

FIGS. 4A, 4B, and 4C are diagrams schematically illustrating light transmission amounts depending on the bending of the optical fiber. Here, FIG. 4A illustrates the light transmission amount obtained when the optical fiber bends on a side on which the detection target portion 211A is provided, FIG. 4B illustrates the light transmission amount obtained when the optical fiber does not bend, and FIG. 4C illustrates the light transmission amount obtained when the optical fiber bends on a side opposite to the side on which the detection target portion 211A is provided. As illustrated in FIGS. 4A, 4B, and 4C, the largest light transmission amount is obtained when the optical fiber bends on a side on which the detection target portion 211A is provided, the second largest light transmission amount is obtained when the optical fiber does not bend, and then the smallest light transmission amount is obtained when the optical fiber bends on a side opposite to the side on which the detection target portion 211A is provided, in this order. Accordingly, a light intensity, which is emitted from the optical fiber, is measured, and thereby it is possible to detect a bending amount in the detection target portion 211A. Since a position on the optical fiber in the radial direction thereof, at which the detection target portion 211A is provided, and an orientation of the detection target portion 211A is already known, it is also possible to find a bending direction and it is possible to detect a bending shape using the bending direction and the bending amount.

In addition, the absorption-wavelength-specific-region generating member 2115 provided in the detection target portion 211A of the optical fiber has an absorption spectrum as illustrated in FIG. 5B with respect to light from an ideal light source having a substantially even light spectrum between wavelength bands $\lambda L$ and $\lambda U$ as illustrated in FIG. 5A. Here, W is an emission wavelength region of the ideal light source. When the light from the ideal light source reaches the absorption-wavelength-specific-region generating member 2115, the absorption-wavelength-specific-region generating member 2115 absorbs, at a rate of the absorption spectrum, light in contact the core 2111 and further evanescent light leaking to the clad 2112 or leaking light, and residual light returns to the core 2111. FIG. 3B illustrates an image drawn for easy understanding. Solid arrows represent light supplied from the light source, the light reaching the detection target portion 211A is absorbed in an absorption spectrum which is specific to the detection target portion, and residual light represented by dotted arrows returns to the core 2111.

Effects of the detection target portion 211A are as follows. It is possible to remove light having an angle larger than a critical angle formed due to a core-clad refractive index difference obtained when the optical fiber bends, and it is possible to control the light by adjusting a reflective index of the clad 2112 with respect to a reflective index $n1$ of the core 2111 such that the reflective index of the clad is lower than the reflective index $n1$ of the core. As in the spectrum illustrated in FIG. 5C, the substantially even light supplied from the light source has a spectrum obtained by receiving an optical effect from the absorption spectrum of the detection target portion 211A.

Accordingly, light intensities are measured in front and rear of the absorption-wavelength-specific-region generating member 2115 of the detection target portion 211A, and thereby it is possible to detect a change in the bending amount in the region of the detection target portion 211A. At this time, when the light intensity for a wavelength, at which the light intensity significantly changes, is particularly measured, it is possible to detect a change in the bending amount of the region of the detection target portion 211A with higher resolution.

Therefore, the fiber sensor 21 includes the light source 212 that causes the light to be incident to the optical fiber as the light guiding member 211, and the light detector 213 that detects the light emitted from the optical fiber. Here, as a configuration of the fiber sensor 21, two transmission type and reflection type are employed.

As illustrated in FIG. 6A, the transmission type has a configuration in which light is supplied to the optical fiber from the light source 212 disposed at one end of the optical fiber as the light guiding member 211, the light guided to the optical fiber receives optical effects from the absorption-wavelength-specific-region generating member 2115 of the detection target portion 211A formed at a position on the optical fiber, and the light detector 213 disposed on the other end of the optical fiber receives light that reaches the detector after transmitting through the optical fiber. As described above, in the transmission type, the light source 212 and the light detector 213 are disposed to be distributed at both sides of the optical fiber. Note that the bending amount, which is obtained using the light intensity detected by the light detector 213, is obtained in relation to not only the region in which the detection target portion 211A is disposed, but also a measurement range L having a predetermined length, which includes the detection target portion 211A.

By comparison, as illustrate in FIG. 6B, the reflection type has a configuration in which the light source 212 and the light detector 213 are disposed on the same side of the optical fiber as the light guiding member 211, a reflective member 216 is provided at the other end of the optical fiber, light, which is incident from the one end of the optical fiber, is reflected from the reflective member 216, and then the light is emitted from the one end of the optical fiber. Therefore, the light source 212 and the light detector 213 are optically connected to the one end of the optical fiber via the light branching unit 214. The light branching unit 214 is an optical distributor (optical coupler), a half mirror, a beam splitter, or the like, and here a light branching unit having two by two ports is used. An antireflective member 215A as the light-source monitoring unit and/or antireflective member 215 is optically connected to the remaining port to which the light source 212, the light detector 213, and the optical fiber as the light guiding member 211 are not optically connected. In addition, the reflective member 216 is a mirror formed with the optical fiber which is vapor-deposited with aluminum. In other words, the reflective member 216 causes light supplied from the light source 212, which reaches the end of the optical fiber through the detection target portion 211A, to return to the light detector 213 side.

Hence, in the reflection type fiber sensor 21, the light from the light source 212 branches by the light branching unit 214 and is incident to the one end of the optical fiber and to the antireflective member 215A. The light supplied to and guided through the optical fiber receives optical effects by the absorption-wavelength-specific-region generating member 2115 of the detection target portion 211A provided at the position on the optical fiber, and is reflected from the reflective member 216 disposed at the other end of the optical fiber. The reflected light is return light guided through the optical fiber in the opposite direction, again receives the optical effects by the absorption-wavelength-specific-region generating member 2115 of the detection target portion 211A, and then is emitted from the one end of the optical fiber. The return light emitted from the optical fiber is incident to the light branching unit 214, branches by the light branching unit 214, and is incident to the light source 212 and the light detector 213. The light detector 213 detects the light intensity of the incident return light. An output signal of the light detector 213 is transmitted to the signal processing unit 22. Note that, although not particularly illustrated, a condenser lens may be disposed between the light branching unit 214 and the one end of the optical fiber. In this case, the light from the light branching unit 214 is condensed by the condenser lens and is incident to the one end of the optical fiber, or the return light from the one end of the optical fiber is collimated into parallel light by the condenser lens and then is incident to the light branching unit 214.

Note that the other return light emitted from the optical fiber, which branches by the light branching unit 214 and is incident to the light source 212, does not have effects on the light source 212 and thus is negligible. In addition, since the other light from the light source 212, after branching by the light branching unit 214, is incident to the antireflective member 215A, the light is not incident to the light detector 213 and thus does not have effects on the detection by the light detector 213. In addition, as the light-source monitoring unit and/or antireflective member 215, not only the antireflective member 215A, but also the light-source monitoring unit may be provided. The light-source monitoring unit may detect the light from the light source 212, which has branched and has been incident, and thereby it is possible to perform feedback control of an emitted light quantity from the light source 212. It is needless to say that it is more desirable that both of the light-source monitoring unit and the antireflective member 215A are provided such that light, which is not incident to the light-source monitoring unit, is not reflected and does not have effects on the light detector 213.

In addition, the light branching unit 214 may also be provided between the light source 212 and the optical fiber in the transmission type fiber sensor 21, and the light from the light source 212, which has branched, may be incident to the light-source monitoring unit and/or antireflective member 215.

In addition, it is possible to provide a plurality of detection target portions 211A. FIG. 7A illustrates the transmission type fiber sensor 21 having two of a first detection target portion 211A1 and a second detection target portion 211A2. In this example, a measurement range L1 and a measurement range L2 are separated from each other; however, the first and second detection target portion 211A1 and 211A2 may be disposed such that the measurement ranges are adjacent to each other. In addition, FIG. 7B illustrates the reflection type fiber sensor 21 having n detection target portions 211A of first to n-th detection target portions 211A1 to 211An.

Here, in the case where the plurality of detection target portions 211A are provided, the detection target portions may be arranged not only along the longitudinal axis of the optical fiber as illustrated in FIGS. 7A and 7B, but also another detection target portion (j-th detection target portion 211Aj) may be provided to have an orientation with a different axis in an orthogonal direction or the radial direction, substantially at the same position along the longitudinal axis, with respect to one detection target portion (i-th detection target portion 211Ai), as illustrated in FIG. 8. In this structure, it is possible to detect not only the bending amount, but also a direction of the bending in the measurement range corresponding to the detection target portion.

Note that the absorption-wavelength-specific-region generating member 2115 may be exposed as it is as illustrated in FIGS. 3A and 3B; however, a region, in which the jacket 2113 and the clad 2112 on the absorption-wavelength-specific-region generating member 2115 are removed, may be filled with a detection-target-portion protective member 2116 instead of the jacket-shaped member such that the optical fiber may be restored to have the original shape as the i-th detection target portion 211Ai illustrated in FIG. 8. Otherwise, as the j-th detection target portion 211Aj illustrated in FIG. 8, the absorption-wavelength-specific-region generating member 2115 may be formed to fill the region formed by removing the jacket 2113 and the clad 2112, and thereby the optical fiber may be restored to have the original shape.

In the case where the optical fiber as the light guiding member 211 is provided with the plurality of the detection target portions 211A, for example, n detection target portions of first to n-th detection target portions 211A1 to 211An as illustrated in FIG. 7B, optical effects obtained by the detection target portions 211A need to be separately detected, in order to detect the bending amount and the bending direction of the measurement range corresponding to the detection target portions 211A.

Therefore, the absorption-wavelength-specific-region generating members 2115 in the detection target portions 211A have different absorption spectra, respectively. Although this will be described below, only two of the i-th detection target portion 211Ai and the j-th detection target portion 211Aj are described as examples, for simplification.

FIG. 9A is a diagram illustrating the absorption spectrum of light of the absorption-wavelength-specific-region generating members 2115 set in the two detection target portions 211Ai and 211Aj, in which a solid line represents the i-th detection target portion 211Ai, and a dashed line represents the j-th detection target portion 211Aj. For example, in a case where the ideal light having the spectrum as illustrated in FIG. 5A is incident, the light intensity is attenuated at a spectral ratio of the solid line and the dashed line illustrated in FIG. 9A in the absorption-wavelength-specific-region generating member 2115 of the detection target portions 211Ai and 211Aj. The absorption wavelength specific regions are positions of $\lambda 1$ and $\lambda 2$ in FIG. 9A, for example. In the regions of $\lambda 1$ and $\lambda 2$, the different detection target portions 211Ai and 211Aj have different absorption rates a, respectively. In the spectrum of the i-th detection target portion 211Ai, the absorption rate is $\alpha 1i$ during $\lambda 1$ and the absorption rate is $\alpha 2i$ during $\lambda 2$. In the spectrum of the j-th detection target portion 211Aj, the absorption rate is $\alpha 1j$ during $\lambda 1$ and the absorption rate is $\alpha 2j$ during $\lambda 2$. $\alpha 1i$ and $\alpha 1j$, and $\alpha 2i$ and $\alpha 2j$ represent different absorption rates for a wavelength $\lambda 1$ and a wavelength $\lambda 2$, and are characterized by different ratios of the absorption rates. As described above, the absorption wavelength specific region means a region in which the detection target portions 211A having such $\lambda 1$ and $\lambda 2$ of the used wavelength bands are characterized by the ratio of the absorption rates of the plurality of wavelengths. The wavelengths $\lambda 1$ and $\lambda 2$ may be specific wavelengths, and may have a width in the wavelength band as illustrated in FIG. 9B.

Separation of the detection target portions 211A is performed by establishing and solving an expression in which a difference between a light intensity of the light source 212 and a light intensity detected by the light detector 213 is equal to a total value to which a change corresponding to each bending amount is given while an intensity ratio of the absorption wavelength specific region of the detection target portions 211A is maintained. Accordingly, it is preferable that the number of the absorption wavelength specific regions is larger than the number of the detection target portions.

Next, the light source 212 will be described. Examples of the light source 212 can include a laser diode (LD), an LED, a lamp, light that emits fluorescent substances by the light described above, and light (for example, white light) having wavelength characteristics necessary for the fiber sensor 21 is collimated and emitted by combining the plurality of light sources. Note that the light source as a term described here also includes a lens system that condenses light and cause the light to be incident to a fiber of fiber coupler in a case where the light branching unit 214 is the fiber coupler. In a case where the light branching unit 214 is a half mirror or a beam splitter, the lens system that collimate the light into parallel light is also included as an example of the light source. Further, in a case where the return light such as the laser diode has effects on an output, an isolator is also included as an example of the light source.

The light source 212 needs to include at least a part of the absorption wavelength specific region. Specifically, as illustrated in FIG. 10A, in a case where two detection target portions 211A are provided, the light source 212 can be a light source that synthesizes and emits relatively narrow band light as including the absorption wavelength specific regions $\lambda 1$ and $\lambda 2$. An example of the light source 212 in this case includes the LED, the LD, or the like. In addition, as illustrated in FIG. 10B, a light source, which causes fluorescent substances to be excited with light having a low wavelength and emits the generated light, may be included as an example of the light source. When the light has such spectrum, it is possible to easily include a plurality of absorption wavelength specific regions. In addition, in the case where the absorption wavelength specific regions $\lambda 1$ and $\lambda 2$ have widths in the wavelength band as in FIG. 9B, the light source 212 may include a part of the plurality of absorption wavelength specific regions as illustrated in FIG. 10C. It is desirable to use a light source that emits light having substantially even spectral characteristics in the plurality of absorption wavelength specific regions as illustrated in FIG. 10D, as light that is easily detected. Preferably in the case of such a light source, there is less possibility that variations are produced in detection accuracy.

In addition, examples of the light source 212 may include not only the light source, which synthesizes and emits the relatively narrow band light as illustrated in FIG. 10A, may be used, but also a plurality of light sources which are caused to emit light having discrete wavelengths in order and supply the light to the optical fiber as the light guiding member 211, as illustrated in FIGS. 11A and 11B. In this manner, a detection band D of the light detector 213 may be able to detect light having wavelengths of the entire absorption wavelength specific region, and there is no need to use a device such as an optical spectroscope that separates and detects the light intensities for each wavelength. In such as configuration, it is possible to very decrease costs of the light detector 213.

It is needless to say that any light detector 213 may be used as long as it is possible to detect characteristics of the absorption wavelength specific region associated with the detection target portion 211A. When a configuration of the light detector 213 is described on the basis of the wavelength band, as illustrated in FIG. 12A, the light detector is characterized in that it is possible to detect two bands of the bands D1 and D2 corresponding to the absorption wavelength specific regions or including the absorption wavelength specific regions in the case where the two detection target portions 211A are provided. The band of the detection may not include all, but the characteristics of the absorption wavelength specific region may remain. For example, the wavelength regions having the characteristics of the absorption wavelength specific region are all included in a case where the three detection target portions 211A are provided; however, as illustrated in FIG. 12B, bands D1, D2, and D3 of the light detector 213 may include bands overlapping each other.

Note that, as a configuration in which optical effects are applied to the detection target portion 211A, a method, in which the absorption-wavelength-specific-region generating member 2115 as described above is not used, may be employed. Further, the absorption-wavelength-specific-region generating member 2115 described above and another method may be combined. When the combination thereof is used, the number of the detection target portions 211A can be increased. In other words, the detection target portion 211A is not limited to the configuration in which the light transmission amount as the optical characteristic of the optical fiber is changed, and, for example, a state of light such as a spectrum or a polarized wave may be changed. In addition, the light detector 213 may detect the light intensity as described above, for example, the optical characteristics corresponding to the state of light such as the spectrum or the polarized wave.

For example, as illustrated in FIG. 13A, the detection target portion 211A is provided with a light emitting body such as a fluorescent member 2117, instead of the absorption-wavelength-specific-region generating member 2115. As illustrated in FIG. 13B, the fluorescent member 2117 has characteristics of absorbing light on short wavelength side as represented by a solid line and emitting light on long wavelength side as represented by dashed lines. In the case of using such a fluorescent member 2117, a method of converting light is different from that of the absorption-wavelength-specific-region generating member 2115, the light reaching the detection target portion 211A is absorbed, and the detection target portion 211A emits scattering light. An emitted light quantity changes depending on the bending direction and the bending amount because an amount of light reaching the fluorescent member 2117 increases and decreases the bending amount of bending. In the case of using such a fluorescent member 2117, the detection sensitivity is slightly degraded in some cases, compared to a case where the absorption-wavelength-specific-region generating member 2115 is used.

In addition, instead of the absorption-wavelength-specific-region generating member 2115, a stacked dielectric membrane may be provided. For example, FIG. 14 illustrates the optical fiber as the light guiding member 211 that is provided with a first absorption-wavelength-specific-region generating member 2115A formed in the first detection target portion 211A1, a stacked dielectric membrane 218 formed in the second detection target portion 211A2, a second absorption-wavelength-specific-region generating member 2115B, which generates a absorption wavelength specific region different from that generated by the first absorption-wavelength-specific-region generating member 2115A, formed in a third detection target portion 211A3, and the fluorescent member 2117 formed in a fourth detection target portion 211A4. Note that a dielectric-membrane effect increasing resin 219 is further formed on the stacked dielectric membrane 218. In FIG. 15, a solid line represents a case where light is incident to the stacked dielectric membrane 218 at a certain incident angle a, a dashed line represents a case where light is incident at an incident angle b different from the incident angle a, and a two-dot chain line represents a case where light is incident at an incident angle c different from the incident angles a and b. As described above, the stacked dielectric membrane 218 has a characteristic of causing a loss of a specific spectrum outside the optical fiber depending on the incident angle of the light, that is, the bending of the optical fiber.

Note that the fiber sensor 21 may be configured of, for example, a method of a fiber Bragg grating (FBG) described in PTL 1, or a method of detecting a wavelength shift of scattering light through Rayleigh scattering or Brillouin scattering and calculating in terms of distortion, in addition to the configuration described above. In a sensor such as the FBG, a spectrum obtained by performing the wavelength shift on an incident spectrum depending on the bending amount returns to the light detector 213 as a reflective wave. Accordingly, the light detector 213 needs to have a sensitivity to the light characteristics (the wavelength and the spectrum) of the optical fiber provided with the detection target portion 211A or to the light from the light source 212.

Next, a configuration of a part other than the fiber sensor 21 of the mobile detection device 2 will be described.

As illustrated in FIG. 1, the signal processing unit 22 includes a control unit 221, a light source control circuit 222, a light detector control circuit 223, a digital conversion unit (A/D) 224, a timing unit 225, a memory 226, an arithmetic processing unit 227, and a communication unit 228.

The control unit 221 is provided with an algorithm installed to control the portions of the signal processing unit 22 and controls the portions in accordance with the algorithm, and thereby preparing a signal that is transmitted to the fixed signal processing device 3. Note that, although the signal will be described below in detail, the signal to be transmitted may be information obtained after conversion by the digital conversion unit 224, or may be bending amount information, detection point position and direction information (shape), a video signal, or the like.

The light source control circuit 222 controls an emitted light quantity and a light emitting timing of the light source 212 of the fiber sensor 21, under the control of the control unit 221. The control of the light source 212 enables a dynamic range of the light detector 213 to be effectively utilized and thus high accuracy and high resolution is achieved. Note that, in a case where the fiber sensor 21 includes a light-source monitoring unit as the light-source monitoring unit and/or antireflective member 215, feedback control is performed on the emitted light quantity from the light source 212 such that a detected light quantity detected in the light-source monitoring unit becomes a predetermined light quantity. In addition, in a case where the light-source monitoring unit is not provided, the light intensity may be detected from the return light obtained when the fiber sensor 21 is in a predetermined state (for example, a straight line state or a state of a circle having a predetermined radius), and the emitted light quantity from the light source 212 may be controlled to be the predetermined light quantity. In this case, the predetermined light quantity may be set to an optimal value with which it is possible to utilize a range of the light detector 213 effectively.

The light detector control circuit 223 controls an operation of the light detector 213 of the fiber sensor 21, under the control of the control unit 221. In other words, the light detector 213 is controlled to perform detection the number of times necessary per second. When the light detector 213 is appropriately controlled, it is possible to more increase a detection speed or to correspond to achieving resolution or accuracy as necessary.

The digital conversion unit 224 is controlled by the control unit 221 and converts, as an analog signal, an output signal of the light detector 213 of the fiber sensor 21 into a digital signal. Note that, in a case where the light detector 213 includes a digital converting function, the signal processing unit 22 may not be provided with the digital conversion unit 224, the control unit 221 may directly control the light detector 213, and thereby a detection value may be received as the digital signal.

The timing unit 225 generates a timing signal that is used in driving the signal processing unit 22, or is used as a communication timing signal by the communication unit 228. An appropriate timing is generated through frequency transformation such as a multiplying process, as necessary.

Note that the timing may be generated by using a signal received by the fixed signal processing device 3.

The memory 226 stores, in a non-volatile manner, fiber sensor individual information as various items of information necessary in order to distinguish the plurality of detection target portions 211A of the fiber sensor 21, or in order to convert the output signal of the light detector 213 of the fiber sensor 21 into another item of information. The fiber sensor individual information is information specific for each fiber sensor 21, and includes sensor information 226A, detection points distinguishing information 226B, detection point position information 226C, shape conversion information 226D, calibration information 226E, or the like. Note that all of the items of information do not need to be stored, and information, which needs to be stored, is determined depending on whether the information is transmitted from the mobile detection device 2 to the fixed signal processing device 3.

Here, the sensor information 226A includes individual identification information (lot No.), history information (using time, repair, or correction information), initial characteristics, or the like in relation to the fiber sensor 21 provided in the mobile detection device 2.

The detection points distinguishing information 226B is detection distinguishing information (including bending state-light spectrum information) of a plurality of detection points necessary for distinguishing each of the distortion or the bending amount, in the plurality of detection target portions 211A provided in the optical fiber as the light guiding member 211 of the fiber sensor 21.

The detection point position information 226C is information of positions of the detection target portions 211A formed in the optical fiber of the fiber sensor 21, or disposition information of the detection target portions 211A with respect to the mounting portion, for example, the insertion portion of the endoscope, of which the bending shape needs to be detected by the fiber sensor system 1. In other words, the detection point position information includes the disposition information and orientation information of at least the one detection target portion 211A.

The shape conversion information 226D is information necessary in a conversion method or conversion necessary when the distortion or the bending amount detected in the detection target portion 211A of the fiber sensor 21 is converted into information in relation to a bending shape such as a shape or a state. Otherwise, the shape conversion information is regulation information (for example, information necessary for conversion calculation such as difficulty in bending or readiness to have a specific shape) of the mobile detection device 2. The regulation information includes information such as bending state-shape conversion information, a detection length, a detection point structure, or a conversion time approximation method. Note that the "state" in the embodiment includes not only a state of a shape such as a straight line or a U shape, but also a state in which normality/abnormality specific for the device equipped with the mobile detection device 2 is determined. The device specific abnormality means a state as referred to as buckling in the field of endoscope, in which the insertion portion that needs to move forward is stopped at a position and a bending shape of the insertion portion changes, and the abnormality varies depending on a use of the device, a service state, a use environment, or the like. In addition, the abnormality includes a motion state such as extension of a subject in a case where the subject has flexibility. The motion of the subject absorbs a force required for the insertion portion to move forward, the insertion portion, which needs to move forward, performs only parallel movement, and thereby a so-called sideslip can occur in which the front end of the insertion portion does not move forward, or the bending shape of the insertion portion does not change. The "state" includes a state of having the motion of the subject. The information in relation to the bending shape can include manipulation support information about supporting insertion manipulation or the like of the device equipped with the mobile detection device 2.

The calibration information 226E includes information about changes depending on a use or elapse of time of the fiber sensor 21, predetermined characteristic change information obtained in a case where characteristics change due to X-ray irradiation or sterilization, information stored during maintenance, or the like.

The arithmetic processing unit 227 is controlled by the control unit 221, and has a function of calculating the distortion and the bending amount of the fiber sensor on the mobile detection device 2 side by using the output signal of the light detector 213 of the fiber sensor 21, which has been converted into the digital signal by the digital conversion unit 224, the sensor information 226A or the detection points distinguishing information 226B stored in the memory 226. In other words, the bending shape of the region, which actually bends, is calculated, based on detection results of the detection target portion 211A. Further, the arithmetic processing unit may have a function of calculating, using the calculated bending shape, information in relation to the bending shape of the fiber sensor 21. In addition, conversion calculation is performed on the signal received by the communication unit 228, by using a predetermined algorithm, and then the arithmetic processing unit can have a function of rewriting the items of information of the memory 226. Note that the arithmetic processing unit 227 can be provided to function as the control unit 221.

The communication unit 228 is a signal transmission/reception module for at least transmitting a signal wirelessly from the mobile detection device 2 to the fixed signal processing device 3. The communication unit 228 may transmit the signal to the fixed signal processing device 3 in one-way communication; however, the communication unit may have a transmitting/receiving function of receiving selection or a request of operation setting or communication content from the fixed signal processing device 3.

The content that is wirelessly transmitted from the mobile detection device 2 to the fixed signal processing device 3 includes final or intermediate processing information in relation to the distortion or the bending amount of at least the fiber sensor 21 or substantially the output information (information obtained by synthesizing signals of the plurality of detection target portions) of the light detector 213, and further various types of information necessary to perform processing of the signal of the fiber sensor 21. Note that the intermediate processing information means information obtained after the signals from the plurality of detection target portions 211A are converted into the distortion or the bending amount (curvature value) of the individual detection target portions 211A1 and 211A2 . . . . In a case where the fiber sensor 21 is a distortion sensor, the plurality of sensors are grouped and a process of detecting a direction of distortion, distinguishing effects of temperature, or the like needs to be performed. In addition, it is possible to include the fiber sensor individual information stored in the memory 226.

In contrast, the fiber sensor individual information may be wirelessly transmitted from the fixed signal processing device 3 to the mobile detection device 2, may be received by the communication unit 228, and may be written and stored in the memory 226. In addition, the reception signal received by the communication unit 228 may be a reset signal for optimizing the detection of the fiber sensor 21.

The monitor 23 is a device on which information in relation to the bending shape of the fiber sensor 21 is displayed, and examples of the monitor may include a light emitting display device such as an LED, as long as the device has a level of displaying normality or abnormality. In addition, in a case where the shape or state of the fiber sensor 21, that is, the shape or state of the subject or the mounting portion of which the bending shape needs to be detected by the fiber sensor system 1 is displayed with characters or pictures, a display device that is capable of displaying the characters or images is mounted.

As described above, the monitor 23 is provided, and thereby whether the fiber sensor 21 normally operates or any abnormality occurs is to be determined. In addition, when the shape or state is displayed as described above, it is possible to use the monitor in an emergency state in a state in which communication to the fixed signal processing device 3 is disconnected.

Note that, instead of the monitor 23, a configuration which is provided with a connector or the like for connecting to an external monitor (not illustrated) disposed outside the mobile detection device 2 and can be connected to the external monitor may be employed.

The power supply unit 24 generates power from a battery such as a primary battery or a secondary battery, or from an electromagnetic wave or a magnetic field through external wireless supply, or using a combination thereof, and supplies the power to the units such that the units of the mobile detection device 2 are driven. It is desirable that the battery is attachable and detachable. This is because, in a case where the mobile detection device 2 is installed in a state in which the battery is not preferably mounted (under a high temperature, high humidity, and a significant pressure change), it is possible to broaden an available range of the device when the battery is mounted in a detachable manner.

Meanwhile, the fixed signal processing device 3 includes a signal processing unit 31, an output unit 32, and a power supply unit 33.

The signal processing unit 31 performs signal processing on a signal wirelessly transmitted from the mobile detection device 2, and converts the signal into information of the bending amount, the bending shape, or the like of the fiber sensor 21. The signal processing unit 31 is provided with a control unit 311, a timing unit 312, a communication unit 313, a memory 314, and an arithmetic processing unit 315.

The control unit 311 is provided with an algorithm installed to control the portions of the signal processing unit 31 and controls the portions in accordance with the algorithm.

The timing unit 312 generates a timing signal that is used in driving the signal processing unit 31, or is used as a communication timing signal by the communication unit 313. An appropriate timing is generated through frequency transformation such as a multiplying process, as necessary.

The communication unit 313 is a signal transmission/reception module for at least receiving a signal of the fiber sensor 21 wirelessly from the mobile detection device 2.

The memory 314 stores mobile transmission information 314A and mobile-side common information 314B. The mobile transmission information 314A is content such as the fiber sensor individual information which is received by the communication unit 313, and can be rewritten and is stored in the memory 314. The mobile-side common information 314B is common to a plurality of mobile detection devices 2 and is stored in the memory 314 in advance in a non-volatile manner.

The arithmetic processing unit 315 performs detection value calculation of the fiber sensor 21, shape conversion or state (state information or the like for determining normality/abnormality specific to the device equipped with the mobile detection device 2) detection, or the like, using the mobile transmission information 314A and the mobile-side common information 314B stored in the memory 314, and calculates and generates information in relation to the bending shape. It is needless to say that calculations performed in the arithmetic processing unit 315 are different depending on whether the content that is transmitted from the mobile detection device 2 is the final or intermediate processing information in relation to the distortion or the bending amount of at least the fiber sensor 21 or substantially the output information (information obtained by synthesizing signals of the plurality of detection target portions) of the light detector 213. Note that the arithmetic processing unit 315 operates at a timing generated in the timing unit 225 of the mobile detection device 2, which is received by the communication unit 313.

The output unit 32 is capable of including a display 321, a memory 322, and a fiber-sensor-system signal transmission unit 323. The display 321 outputs information in relation to the bending shape such as the bending shape or state calculated and generated by the signal processing unit 31. The output of the information in relation to the bending shape is not limited to the display, and may be performed in a method of using a sound, vibration, light, heat, or the like that is discriminable by a human. The memory 322 stores such information. The fiber-sensor-system signal transmission unit 323 transmits, to another system, such information as an output signal S of the fiber sensor system 1. The output unit 32 may include at least one of the display 321, the memory 322, and the fiber-sensor-system signal transmission unit 323.

The power supply unit 33 has a function of converting power W supplied from an AC power supply or a DC power supply into a power source required for the fiber sensor system 1. In a case where the power is wirelessly transmitted to the mobile detection device 2, the power supply unit 33 has a function of generating a signal thereof (an electromagnetic wave or a magnetic field).

In the fiber sensor system having the configuration described above, the output signal of the light detector 213 of the fiber sensor 21, or at least the signal of the intermediate processing information in the signal processing of obtaining the bending shape of at least the one detection target portion 211A using the output signal is wirelessly transmitted from the mobile detection device 2 to the fixed signal processing device 3. The fixed signal processing device 3 obtains and outputs the bending shape of at least the one detection target portion 211A using the signal wirelessly transmitted from the mobile detection device 2.

As described above, the fiber sensor system 1 according to the embodiment includes: the mobile detection device 2 that is provided with the fiber sensor 21; and the fixed signal processing device 3 that performs signal processing on the signal output from the mobile detection device 2. Here, the mobile detection device 2 includes the fiber sensor 21 that is provided with the light source 212 which generates light having at least the wavelength component necessary for detecting the bending shape of at least the one detection target portion 211A, the flexible light guiding member 211 which guides the light from the light source 212 and has at least the one detection target portion 211A, and the light detector 213 which detects light emitted from the light guiding member 211. Further, the mobile detection device 2 includes the signal processing unit 22 as a first signal processing unit that is provided with the communication unit 228 as a first communication unit which wirelessly transmits and receives signals to and from the fixed signal processing device 3, and that wirelessly transmits, by the communication unit 228 to the fixed signal processing device 3, the output signal of the light detector 213 of the fiber sensor 21, or at least the signal of the intermediate processing information in the signal processing of obtaining the bending shape of at least the one detection target portion 211A using the output signal. In addition, the fixed signal processing device 3 includes the signal processing unit 31 as the second signal processing unit that is provided with the communication unit 313 as a second communication unit which wirelessly transmits and receives signals to and from the mobile detection device 2, and that obtains information about the bending shape of at least the one detection target portion 211A using the signal received by the communication unit 313. Further, the fixed signal processing device 3 includes the output unit 32 that outputs the information about the bending shape of at least the one detection target portion 211A, which is obtained by the signal processing unit 31.

Since the light detector 213 picks up the light signal of the fiber sensor 21 as an electrical signal, the electrical signal or at least the signal of the intermediate processing information in the signal processing on the electrical signal is wirelessly transmitted to the fixed signal processing device 3, such a fiber sensor system 1 is not configured to transmit the light signal to an external device through an optical connector. Hence, it is possible to reliably and accurately detect the shape, without an effect of the optical connector region on the light signal from the fiber sensor 21.

Further, since the signal is wirelessly transmitted and received between the mobile detection device 2 and the fixed signal processing device 3, no wire is needed therebetween. Thus, the manipulation or movement of the device provided with the fiber sensor system 1 is highly freely performed, and it is possible to reduce an impact on a human body due to a load or resistance of the wire.

In addition, in the fiber sensor system 1 according to the embodiment, the light guiding member 211 of the fiber sensor 21 is provided with the plurality of detection target portions 211A, and the plurality of detection target portions 211A have different absorption spectra, emission spectra, reflection spectra, or loss spectra, respectively.

Accordingly, in a case where the one light guiding member 211 is provided with the multiple detection target portions 211A, and thus the detection target portions are disposed at narrow intervals, it is possible to more accurately detect a plurality of bending amounts corresponding to the position at which the light guiding member 211 is disposed, in addition to the advantage of the disposition, and it is possible to more accurately detect the shape by applying the amounts to the shape detection using the amounts of bending.

Further, since the one the light guiding member 211 can perform detection with the multiple detection target portions 211A, it is possible to decrease the number of the light sources and the light detectors, and it is possible to decrease the mobile detection device 2 in size such that it is advantageous to achieve mobilization thereof.

In addition, in the fiber sensor system 1 according to the embodiment, the light guiding member 211 of the fiber sensor 21 is the optical fiber, and the plurality of detection target portions 211A have, at least in a layer of the clad 2112 of the optical fiber, different absorption spectra, emission spectra, reflection spectra, or loss spectra, respectively.

Accordingly, it is possible to configure the system without degrading the strength of the optical fiber, compared to a type of fiber sensor in which the core 2111 is processed.

In addition, in the fiber sensor system 1 according to the embodiment, the signal processing unit 22 of the mobile detection device 2 includes the memory 226 that stores the fiber sensor individual information (the sensor information 226A (the individual identification information (lot No.), the history information (using time, repair, or correction information), the initial characteristics) as the information specific for each fiber sensor, the detection points distinguishing information 226B (detection distinguishing information of the plurality of detection points (including change amount information of the bending state-light intensity)), the detection point position information 226C (the disposition information and orientation information of the detection target portions 211A), the shape conversion information 226D (the bending state-shape conversion information, the detection length, the detection point structure, conversion time approximation method, or the like), and the calibration information 226E.

Accordingly, even in a case where the plurality of mobile detection devices 2 are provided with respect to the one fixed signal processing device 3, it is possible to process the output signal of the fiber sensor 21, based on the information suitable for the mobile detection device. Time and effort or maintenance of inputting new information to the fixed signal processing device 3 is not needed and thus the device is more conveniently used.

In addition, in the fiber sensor system 1 according to the embodiment, the signal processing unit 22 of the mobile detection device 2 further wirelessly transmits, to the fixed signal processing device 3, the-fiber sensor individual information by the communication unit 228.

Accordingly, even when the fixed signal processing device 3 does not have the information of the fiber sensor 21, it is possible to convert the distortion or the bending amount detected by the fiber sensor 21 into the bending shape or state (state information for determining the normality/abnormality specific for the device) of the device provided with the fiber sensor 21.

Note that, in the fiber sensor system 1 according to the embodiment, the signal processing unit 22 of the mobile detection device 2 wirelessly transmits, by the communication unit 228 to the fixed signal processing device 3, the fiber sensor individual information, at least one timing of each time the output signal of the light detector 213 or at least the signal of the intermediate processing information is transmitted by the communication unit 228, the time of starting up of the mobile detection device 2 and timing as necessary.

In other words, as illustrated in FIG. 16A, at the time of starting up of the mobile detection device 2, it is possible to transmit the fiber sensor individual information.

Otherwise, as illustrated in FIG. 16B, whenever the output signal of the light detector 213 or the signal of the intermediate processing information is transmitted by the communication unit 228, it is possible to transmit the fiber sensor individual information.

In addition, as illustrated in FIG. 16C, it is possible to transmit the fiber sensor individual information as necessary.

Note that, in a case where the fiber-sensor-individual information is transmitted as necessary, the signal processing unit 22 of the mobile detection device 2 may wirelessly transmit, to the fixed signal processing device 3 by the communication unit 228, the fiber sensor individual information in response to a request from the fixed signal processing device 3, which is received by the communication unit 228.

In this manner, since it is possible to use only the necessary information through the transmission, it is possible to maintain communication at a high speed. Otherwise, it is possible to increase the number of times updating is performed when a shape or the like is obtained.

In addition, in the fiber sensor system 1 according to the embodiment, the signal processing unit 22 of the mobile detection device 2 further includes the digital conversion unit 224 that converts the output signal of the light detector 213 of the fiber sensor 21 into the digital signal, and the arithmetic processing unit 227 that calculates the bending shape or state of at least the one detection target portion of the fiber sensor, based on the digital signal converted by the digital conversion unit 224, and the fiber sensor individual information stored in the memory 226.

As described above, the arithmetic processing is performed on the mobile detection device 2 side, and thereby it is possible to find the state of the mobile detection device 2 when it is not possible to communicate with the fixed signal processing device 3, and it is possible to more appropriately take action (individual operation, maintaining elapsed state, a stop, or the like) to cope with the time of communication failure.

In addition, in the fiber sensor system 1 according to the embodiment, the signal processing unit 22 of the mobile detection device 2 further includes the control unit 221 that controls at least the light source 212 and the light detector 213 of the fiber sensor 21 and the communication unit 228.

Accordingly, the control unit 221 is capable of appropriately controlling the units of the mobile detection device 2. For example, the control of the light source 212 enables the dynamic range of the light detector 213 to be effectively utilized and thus high accuracy and high resolution is achieved. In addition, when the light detector 213 is appropriately controlled, it is possible to more increase the detection speed or to correspond to achieving resolution or accuracy as necessary.

In addition, in the fiber sensor system 1 according to the embodiment, the mobile detection device 2 further includes the power supply unit 24 that generates power from the battery or external wireless supply and supplies the power to the light source 212 and the light detector 213 of the fiber sensor 21 and to the signal processing unit 22.

Accordingly, no cable for power supply to the mobile detection device 2 is needed, either, and thus, the manipulation or movement of the device provided with the fiber sensor system 1 is highly freely performed, and it is possible to reduce an impact on a human body due to a load or resistance of the cable Note that it is desirable that the mobile detection device 2 enters a power saving mode in the case where suppliable power of the power supply unit 24 decreases to be small.

For example, when a power detecting unit (not illustrated) detects the suppliable power of the power supply unit 24, and the suppliable power of the power supply unit 24 is lowered to a predetermined threshold value 1, as illustrated in FIG. 17, the control unit 221 of the signal processing unit 22 causes the mobile detection device 2 to enter the power saving mode, and notification of insufficient power is transmitted to the fixed signal processing device 3 by the communication unit 228. Details of the power saving mode include lowering of a transmission frequency, stop of the arithmetic processing unit 227, lowering of light quantity of the light source 212, stop of the monitor 23 that operates with the power, or the like.

When the suppliable power of the power supply unit 24 is lowered to a predetermined threshold value 2, the control unit 221 of the signal processing unit 22 transmits the stop signal to the fixed signal processing device 3 by the communication unit 228, and causes the mobile detection device 2 to stop operation.

In this manner, even when suppliable power of the power supply unit 24 decreases to be small, it is possible to continue the operation of the mobile detection device 2 at the lowermost level as the power saving mode.

In addition, in the fiber sensor system 1 according to the embodiment, the mobile detection device 2 includes the monitor 23 that displays the state of the fiber sensor 21, or a terminal for connecting such a monitor.

In this manner, whether the fiber sensor 21 normally operates or any abnormality occurs is to be determined. In addition, when the shape or state is displayed as described above, it is possible to use the monitor in an emergency state in which communication to the fixed signal processing device 3 is disconnected.

In addition, the fiber sensor system 1 according to the embodiment can be installed in the endoscope device. Note that, in the specification, the endoscope device is not limited to a medical endoscope or to an industrial endoscope, and is a device that includes an insertion portion which is inserted into the insertion target body, such as forceps or a catheter.

Hereinafter, an example of the medical endoscope as the endoscope device will be described. In other words, as illustrated in FIG. 18, an endoscope device 4 includes an insertion portion 41 that is inserted into the insertion target body, and a manipulation unit 42 that is integrally configured with the insertion portion 41. The insertion portion 41 is a flexible tubular member and can be inserted into the inside of the insertion target body from an insertion opening of the insertion target body. Although not particularly illustrated, an image opening and an illumination light emitting portion are provided at the end portion (hereinafter, referred to as an insertion-portion front end) of the insertion portion 41 in an inserting direction, and an imaging unit is internally provided in the vicinity of the insertion-portion front end inside the insertion portion 41. Illumination light emitted from the illumination light emitting portion is reflected from the inside of the insertion target body and is incident to the imaging opening, and the imaging unit receives light incident to the imaging opening and performs imaging. An image captured by the imaging unit is output to a display 44 through a video processor 43.

In addition, the insertion portion 41 has a bending portion in the vicinity of the insertion-portion front end. The bending portion is connected to a wire and a manipulation knob 421 provided in the manipulation unit 42. In this manner, movement of the manipulation knob 421 causes the wire to be pulled and it is possible to manipulate the bending of the bending portion.

In a case where the endoscope device 4 is equipped with the fiber sensor system 1 according to the embodiment, the mobile detection device 2 is mounted on the insertion portion 41 and the manipulation unit 42. In addition, the fixed signal processing device 3 is provided with the built-in video processor 43, and the display 44 is connected to the fixed signal processing device 3.

In other words, the light guiding member 211 of the fiber sensor 21 is disposed to extend in the longitudinal axis direction of the insertion portion 41, and the light source 212 and the light detector 213 of the fiber sensor 21 are internally provided in the manipulation unit 42. In addition, the signal processing unit 22 and the power supply unit 24 are internally provided in the manipulation unit 42.

Note that, in this example, the manipulation unit 42 is not connected to the video processor 43 through a wire. Therefore, the manipulation unit 42 is further provided with a built-in illuminating light source 422, and light emitted from the illuminating light source 422 is guided by an illuminating light guiding path (not illustrated) in the insertion portion 41 and is to be emitted as the illumination light from the illumination light emitting portion in the vicinity of the insertion-portion front end.

In addition, since the manipulation unit 42 and the video processor 43 are not connected through a wire, the image captured by the imaging unit is transmitted to the fixed signal processing device 3 by the communication unit 228 of the signal processing unit 22.

Note that the communication unit 228 includes a communication unit-dedicated processing circuit 2281 and a signal antenna 2282. The communication unit-dedicated processing circuit 2281 performs modulation or encoding on the signal from the control unit 221, and performs decoding or demodulation on the signal from the fixed signal processing device 3, which is received by the signal antenna 2282.

In addition, the power supply unit 24 includes a power antenna 241. Note that the signal antenna 2282 may serve as the power antenna 241.

Similarly, in the fixed signal processing device 3, the communication unit 313 of the signal processing unit includes a communication unit-dedicated processing circuit 3131 and the signal antenna 3132, and the power supply unit 33 also includes a power antenna 331. Similarly, the signal antenna 3132 may serve as the power antenna 331.

The signal processing unit 31 transmits the image received by the communication unit 313 to the video processor 43. The output unit 32 transmits, by the fiber-sensor-system signal transmission unit 323 to the display 44, the information about the bending shape or state, as the output signal S, which is calculated and generated in the signal processing unit 31, then the information is displayed on the display, and the image processed in the video processor 43 is transmitted to the display 44, and the image is displayed on the display. The display on the display 44, as the output signal S and the image, may be performed by displaying in windows disposed side by side, or may be switch and displayed. In addition, in this case, the output unit 32 may not have the display 321. Otherwise, the display 321 may output information in relation to the bending shape such as the bending shape or state calculated and generated by the signal processing unit 31, in a method using a sound, vibration, light, heat, or the like that is discriminable by a human, other than the display.

As described above, the endoscope device 4 is equipped with the fiber sensor system 1 according to the embodiment, and thereby it is possible to reliably and highly accurately detect the shape of the insertion portion 41.

In addition, in the fiber sensor system 1 according to the embodiment, the communication unit 313 of the fixed signal processing device 3 includes at least the one signal antenna 3132 as a wireless signal antenna. The signal antenna 3132 may serve as the power antenna.

In addition, in the fiber sensor system 1 according to the embodiment, the communication unit 313 of the fixed signal processing device 3 includes at least the one signal antenna 3132 as the wireless signal antenna and the power antenna 331 as the wireless power supply antenna.

In this manner, it is possible to provide an appropriate wireless communication environment. It is possible to employ the optimal configuration corresponding to a difference in the frequencies and a difference in communication methods. In addition, there is no need to distinguish the signal from the power, and thus power consumption efficiency on the mobile detection device 2 side increases.

Note that, as illustrated in FIG. 19, the manipulation unit 42 and the video processor 43 may be connected through a wire, as it is, such that the existing configuration of the endoscope device 4 is not changed. In this case, the illuminating light source device or the-like 431 can include the built-in video processor 43. In addition, since it is possible to supply the power from the video processor 43, the power supply unit 24 of the mobile detection device 2 may not include the built-in manipulation unit 42.

Otherwise, as illustrated in FIG. 20, a configuration, in which the mobile detection device 2 is fixed (may use a member that easily peels off, or may use a tie, other than strong fixing using a screw or adhesion) to part of the existing manipulation unit 42 of the endoscope device 4, may be employed. In this case, the light guiding member 211 is used by being inserted into a forceps channel 411 which is provided in the insertion portion 41.

In addition, in a case where the power supply unit 24 is configured to generate power from the battery, as illustrated in FIG. 21A, the power supply unit 24 connects, via a contact point 244, the battery 242 and a power conversion unit 243 that generates power through power supply from the battery. However, as illustrated in FIG. 21B, the power supply unit 24 may be provided with the power conversion unit 243 that generates the power though contactless supply from the battery 242. In other words, a configuration of short-distance wireless power supply from the battery 242 may be employed.

In addition, in a case where the power supply unit 24 is configured to generate power by combining supply from the battery 242 and wireless power supply from the power supply unit 33 of the fixed signal processing device 3, it is possible to charge the battery 242 with the power generated through the wireless power supply.

In this case, as illustrated in FIG. 22, the wireless power supply is performed in the standby state of the mobile detection device 2 in which the mobile detection device 2 is not used, and the signal transmission by the communication unit 228 is performed in an operation state of the mobile detection device 2. As described above, the wireless power supply and the signal transmission are performed at different timings.

Note that, in a case where the power supply unit 24 is not provided with the battery 242, and is configured to generate the power using only the wireless power supply from the power supply unit 33 of the fixed signal processing device 3, as illustrated in FIG. 23, the wireless power supply is not performed in the standby state of the mobile detection device 2 in which the mobile detection device 2 is not used, but is performed in the operation state of the mobile detection device 2. The signal transmission by the communication unit 228 is performed only when the power supply unit 24 generates the power through the wireless power supply.

As described above, the present invention is described, based on the embodiment; however, the present invention is not limited to the embodiments described above, and it is needless to say that it is possible to perform various modifications and applications within a range of the gist of the present invention.

Example embodiments of the present invention relate to a fiber sensor system. The fiber sensor system comprises a detection device that is provided with a fiber sensor and a signal processing device that performs signal processing on a signal output from the detection device.

The detection device includes a fiber sensor that is provided with a light source that generates light having at least a wavelength component necessary for detecting a bending shape of at least one detection target portion, a flexible light guiding member which guides the light from the light source and has at least the one detection target portion, and a light detector which detects light emitted from the light guiding member, and a first signal processing unit that is provided with a first communication unit which wirelessly transmits and receives signals to and from the signal processing device, and that wirelessly transmits, by the first communication unit to the signal processing device, an output signal of the light detector of the fiber sensor, or at least a signal of intermediate processing information in signal processing of obtaining a bending shape of at least the one detection target portion using the output signal.

The signal processing device includes a second signal processing unit that is provided with a second communication unit which wirelessly transmits and receives signals to and from the detection device, and that obtains information about the bending shape of at least the one detection target portion using the signal received by the second communication unit, and an output unit that outputs the information about the bending shape of at least the one detection target portion, which is obtained by the second signal processing unit.

The light guiding member of the fiber sensor can have a plurality of detection target portions.

The plurality of detection target portions can have different absorption spectra, emission spectra, reflection spectra, or loss spectra, respectively.

The light guiding member of the fiber sensor can be an optical fiber.

The plurality of detection target portions can have, at least in clad layer of the optical fiber, different absorption spectra, emission spectra, reflection spectra, or loss spectra, respectively.

The first signal processing unit of the detection device can be provided with a memory that stores fiber sensor individual information as information which is specific for each fiber sensor.

The first signal processing unit of the detection device can further wirelessly transmit, to the signal processing device, the-fiber sensor individual information by the first communication unit.

The first signal processing unit of the detection device can wirelessly transmit, by the first communication unit to the signal processing device, the fiber sensor individual information, at least one timing of each time the output signal of the light detector or at least the signal of intermediate processing information is transmitted by the first communication unit, the time of starting up of the detection device and timing as necessary.

The first signal processing unit of the detection device can wirelessly transmit, to the signal processing device by the first communication unit, the fiber sensor individual information in response to a request from the signal processing device, which is received by the first communication unit.

The first signal processing unit of the detection device can be further provided with a digital conversion unit that converts the output signal of the light detector of the fiber sensor into a digital signal, and an arithmetic processing unit that calculates a bending shape or state of at least the one detection target portion of the fiber sensor, based on the digital signal converted by the digital conversion unit, and the fiber sensor individual information stored in the memory.

The first signal processing unit of the detection device can be further provided with a control unit that controls at least the light source and the light detector of the fiber sensor and the first communication unit.

The detection device can be further provided with a power supply unit that generates power from a battery and/or external wireless supply and supplies the power to the light source and the light detector of the fiber sensor and to the first signal processing unit.

The detection device can enter a power saving mode in a case where suppliable power of the power supply unit decreases to be small.

The second communication unit of the signal processing device can be provided with at least one radio signal antenna.

The second communication unit of the signal processing device can be provided with at least both of one radio signal antenna and one wireless power supply target antenna.

The power supply unit can be provided with a power conversion unit that generates the power though contactless supply from the battery.

The power supply unit can perform the external wireless supply in a standby state of the detection device in which the detection device is not used.

The first communication unit can perform the wireless transmission in a state in which the detection device is used.

The detection device can be provided with a monitor that displays a state of the fiber sensor, or a terminal for connecting such a monitor.

Example embodiments of the present invention relate to an endoscope device that is equipped with the fiber sensor system.

The device comprises an insertion portion that is inserted into an insertion target body.

The light guiding member of the fiber sensor is disposed to extend in a longitudinal axis direction of the insertion portion.

What is claimed is:

1. A fiber sensor system comprising:
 a mobile detection device having;
  a light source;
  a light guide configured to guide a light from the light source, the light guide having a plurality of detection target configured to provide optical effect on the light in accordance with a bend state of the light guide;
  a light detector configured to detect the light emitted from the light guide and provide information of the detected light; and
  a first communication unit configured to transmit wirelessly the information of the detected light so as to eliminate a wire connection and to enable the mobile detection device to be operated wirelessly, and thereby eliminating a loss of a light and detecting a minute change to the light during an operation of the mobile detection device.

2. The fiber sensor system of claim 1 further comprising:
 a memory enabled to store an individual information of the fiber sensor, wherein the fiber sensor comprises the light source, the light guide and the light detector, and wherein the individual information of the fiber sensor is used for calculating the bend state.

3. The fiber sensor system of claim 2, wherein the first communication unit configured to transmit wirelessly the individual information stored in the memory, and the fiber sensor system further comprising:
a second communication unit configured to receive wirelessly the information of the detected light and the individual information of the fiber sensor from the first communication unit; and
a processor enabled to calculate the bend state of the light guide based on the information of the detected light and the individual information.

4. The fiber sensor system of claim 1, further comprising:
a second communication unit configured to receive wirelessly the information of the detected light from the first communication unit; and
a processor enabled to calculate the bend state of the light guide based on the information of the detected light.

5. The fiber sensor system of claim 4, wherein the second communication unit is disposed in a fixed signal processing device.

6. The fiber sensor system of claim 1 is configured to be disposed in an endoscope having an insertion portion and a manipulator attached with one another.

7. The fiber sensor system of claim 6 wherein the mobile detection device is configured to be disposed in the insertion portion and/or the manipulator.

8. A fiber sensor system comprising:
a mobile detection device having;
a light source;
a light guide configured to guide a light from the light source, the light guide having a plurality of detection target configured to provide optical effect on the light in accordance with a bend state of the light guide;
a light detector configured to detect the light emitted from the light guide and provide information of the detected light;
a first processor enabled to calculate an intermediate processing information relating to the bend state of the light guide; and
a first communication unit configured to transmit wirelessly the intermediate processing information to a fixed signal processing device so as to enable the mobile detection device to be operated wirelessly, and thereby eliminating a loss of a light and detecting a minute change to the light during an operation of the mobile detection device.

9. The fiber sensor system of claim 8 further comprising:
a memory enabled to store an individual information of the fiber sensor,
wherein the fiber sensor comprises the light source, the light guide and the light detector, and
wherein the individual information of the fiber sensor is used for calculating the bend state.

10. The fiber sensor system of claim 9, wherein the first communication unit configured to transmit wirelessly at least of a part of the individual information stored in the memory, and the system further comprising:
a second communication unit configured to receive wirelessly the intermediate processing information and at least the part of the individual information of the fiber sensor from the first communication unit; and
a second processor enabled to calculate the bend state of the light guide based on the intermediate processing information and the individual information.

11. The fiber sensor system of claim 8 further comprising:
a second communication unit configured to receive wirelessly the intermediate processing information from the first communication unit; and
a second processor enabled to calculate the bend state of the light guide based on the intermediate processing information.

12. A fiber sensor system comprising:
a mobile detection device having;
a light source;
a light guide configured to guide a light from the light source, the light guide having a plurality of detection target configured to provide optical effect on the light in accordance with a bend state of the light guide;
a light detector configured to detect the light emitted from the light guide and provide information of the detected light;
a first processor enabled to calculate the bend state of the light guide based on the detected light; and
a first communication unit configured to transmit wirelessly the bend state of the light guide so as to eliminate a wire connection and to enable the mobile detection device to be operated wirelessly, and thereby eliminating a loss of a light and detecting a minute change to the light during an operation of the mobile detection device.

13. The fiber sensor system of claim 12 further comprising:
a memory enabled to store an individual information of the fiber sensor,
wherein the fiber sensor comprises the light source, the light guide and the light detector; and
wherein the individual information of the fiber sensor is used for calculating the bend state, and
wherein the first processor is enabled to calculate the bend state of the light guide based on the detected light and the individual information of the fiber sensor.

14. A fiber sensor system used in an endoscope having an insertion portion and a manipulator being attached with one another, the fiber sensor system comprising:
a mobile detection device configured to be disposed in the insertion portion and/or the manipulator wherein the mobile detection device having
a light source;
a light guide configured to guide a light from the light source, the light guide having a plurality of detection target configured to provide optical effect on the light in accordance with a bend state of the light guide;
a light detector configured to detect the light emitted from the light guide and provide information of the detected light;
a first processor enabled to calculate an intermediate processing information relating to the bend state of the light guide;
a second processor enabled to calculate the bend state of the light guide based on the intermediate processing information; and
a first communication unit configured to transmit wirelessly the bend state of the light guide to a fixed signal processing device so as to enable the mobile detection device to be operated wirelessly, and thereby eliminating a loss of a light and detecting a minute change to the light during an operation of the mobile detection device.

15. The fiber sensor system of claim 14 further comprising:
a memory enabled to store an individual information of the fiber sensor, wherein the fiber sensor comprises the light source, the light guide and the light detector, and wherein the individual information of the fiber sensor is used for calculating the bend state.

16. The fiber sensor system of claim 14, further comprising:

a second communication unit disposed in the fixed signal processing device and configured to receive wirelessly the bend state of the light guide from the first communication unit.

* * * * *